US010612003B2

(12) United States Patent
Yliperttula et al.

(10) Patent No.: US 10,612,003 B2
(45) Date of Patent: Apr. 7, 2020

(54) PLANT DERIVED CELL CULTURE MATERIAL

(75) Inventors: Marjo Yliperttula, Espoo (FI); Patrick Laurén, Espoo (FI); Madhushree Bhattacharya, Helsinki (FI); Yanru Lou, Helsinki (FI); Antti Laukkanen, Helsinki (FI)

(73) Assignee: UPM-KYMMENE CORPORATION, Helsinki (FI)

(*) Notice: Subject to any disclaimer, the term of this patent is extended or adjusted under 35 U.S.C. 154(b) by 0 days.

(21) Appl. No.: 13/881,959

(22) PCT Filed: Oct. 26, 2011

(86) PCT No.: PCT/FI2011/050939
§ 371 (c)(1),
(2), (4) Date: Sep. 13, 2013

(87) PCT Pub. No.: WO2012/056109
PCT Pub. Date: May 3, 2012

(65) Prior Publication Data
US 2013/0344036 A1 Dec. 26, 2013

(30) Foreign Application Priority Data
Oct. 27, 2010 (FI) .................. 20106121

(51) Int. Cl.
C12N 5/071 (2010.01)
A61K 47/38 (2006.01)
C08L 1/02 (2006.01)
C12N 5/00 (2006.01)
C12N 11/04 (2006.01)
C12N 11/12 (2006.01)
C08L 97/02 (2006.01)
A61K 47/26 (2006.01)
A61K 9/06 (2006.01)
A61L 27/20 (2006.01)
A61L 27/36 (2006.01)
A61L 27/38 (2006.01)
A61L 27/52 (2006.01)
C08J 3/075 (2006.01)
C12N 5/0735 (2010.01)
C12N 5/079 (2010.01)

(52) U.S. Cl.
CPC .............. C12N 5/0671 (2013.01); A61K 9/06 (2013.01); A61K 47/26 (2013.01); A61K 47/38 (2013.01); A61L 27/20 (2013.01); A61L 27/3637 (2013.01); A61L 27/38 (2013.01); A61L 27/52 (2013.01); C08J 3/075 (2013.01); C08L 1/02 (2013.01); C08L 97/02 (2013.01); C12N 5/0068 (2013.01); C12N 5/0606 (2013.01); C12N 5/067 (2013.01); C12N 5/0621 (2013.01); C12N 5/0672 (2013.01); C12N 11/04 (2013.01); C12N 11/12 (2013.01); C08J 2301/02 (2013.01); C08J 2389/00 (2013.01); C12N 2533/78 (2013.01)

(58) Field of Classification Search
None
See application file for complete search history.

(56) References Cited

U.S. PATENT DOCUMENTS

| 5,254,471 | A | 10/1993 | Mori et al. |
| 5,405,953 | A | 4/1995 | Banker et al. |
| 5,558,861 | A | 9/1996 | Yamanaka |
| 6,602,994 | B1 | 8/2003 | Cash et al. |
| 7,449,180 | B2 | 11/2008 | Kisiday et al. |
| 9,631,177 | B2 | 4/2017 | Yliperttula et al. |
| 2005/0095695 | A1 | 5/2005 | Shindler et al. |
| 2007/0053960 | A1 | 3/2007 | Brown, Jr. et al. |
| 2007/0275458 | A1 | 11/2007 | Gouma |
| 2008/0146701 | A1 | 6/2008 | Sain |
| 2008/0193536 | A1* | 8/2008 | Khademhosseini ......... A61K 35/545 424/486 |
| 2009/0028927 | A1 | 1/2009 | Wan et al. |
| 2009/0305412 | A1 | 12/2009 | Ying |
| 2010/0065236 | A1* | 3/2010 | Henriksson ............ D21C 9/002 162/174 |
| 2010/0172889 | A1 | 7/2010 | Catchmark |
| 2010/0233234 | A1* | 9/2010 | Arinzeh et al. ............ 424/423 |
| 2010/0233245 | A1 | 9/2010 | Narayana |
| 2011/0015387 | A1* | 1/2011 | Schuth .................... C08B 1/003 536/124 |

(Continued)

FOREIGN PATENT DOCUMENTS

| CN | 1730734 A | 11/2005 |
| CN | 1718172 A | 1/2006 |

(Continued)

OTHER PUBLICATIONS

Bodin et al. "Modification of nanocellulose with a xyloglucan-RGD conjugate enhances adhesion and proliferation of endothelial cells: implications for tissue engineering." Biomacromolecules 8(12): 3697-3704, 2007.*
Klemm et al. "Nanocelluloses as innovative polymers in research and application", Advances in Polymer Science 205: 49-96, 2006.*
Henriksson et al. "An environmentally friendly method for enzyme-assited preparation of microfibrillated cellulose (MFC) nanofibers", European Polymer Journal 43: 3434-3441, 2007.*
Sigma "Sigmacell Cellulose type 101 Product sheet", available from company's website, copy right 2015.*
Acumedia "LB Broth, Lennox (7290)", available from company's website, Re. 04, Nov. 2010.*

(Continued)

Primary Examiner — Emily A Cordas
(74) Attorney, Agent, or Firm — Nixon Peabody LLP

(57) ABSTRACT

The present invention relates material that is useful in culturing and transferring cells as well as delivering cells. The material comprises plant derived cellulose nanofibers or derivatives thereof, wherein the cellulose nanofibers are in a form of a hydrogel or membrane. The invention also provides methods for producing these materials and compositions and uses thereof.

18 Claims, 8 Drawing Sheets

(56) References Cited

U.S. PATENT DOCUMENTS

| | | | |
|---|---|---|---|
| 2011/0117319 A1 | 5/2011 | Yano et al. | |
| 2011/0198282 A1 | 8/2011 | Chu et al. | |
| 2013/0011385 A1 | 1/2013 | Li et al. | |

FOREIGN PATENT DOCUMENTS

| | | | |
|---|---|---|---|
| CN | 1973029 | | 5/2007 |
| CN | 101392246 | | 3/2009 |
| CN | 101392246 | A | 3/2009 |
| EP | 2633032 | B1 | 2/2015 |
| EP | 2632493 | B1 | 12/2015 |
| EP | 2633033 | B1 | 4/2016 |
| JP | 2008001728 | | 1/2008 |
| JP | 2008297364 | | 12/2008 |
| JP | 2008308802 | A | 12/2008 |
| JP | 2009502242 | | 1/2009 |
| JP | 2009126837 | | 6/2009 |
| JP | 2009523849 | | 6/2009 |
| JP | 2010007010 | | 1/2010 |
| JP | 2010013604 | | 1/2010 |
| JP | 2011057746 | | 3/2011 |
| WO | WO2004007683 | | 1/2004 |
| WO | 2007/012050 | A2 | 1/2007 |
| WO | WO 2009/095562 | A2 | 8/2009 |
| WO | WO2009126106 | | 10/2009 |
| WO | WO2009126980 | | 10/2009 |
| WO | WO 2010/039865 | A2 | 4/2010 |
| WO | WO2010092239 | | 8/2010 |
| WO | WO2010115785 | | 10/2010 |

OTHER PUBLICATIONS

Abe et al. "Formation of hydrogels from cellulose nanofibers", Carbohydrate Polymers 85 (4): 733-737, available on online Apr. 9, 2011.*

Doheny et al. "Cellulose as an inert matrix for presenting cytokines to target cells: production and properties of a stem cell factor-cellulose-binding domain fusion protein." Biochemical Journal 339. Pt 2 (1999): 429. (Year: 1999).*

Rose et al. "The study of cellulose structure and depolymerization through single-molecule methods." Industrial Biotechnology 11.1 (2015): 16-24. (Year: 2015).*

Evenou F et al: "Microfibrillated cellulose sheets coating oxygen-permeable PDMS membranes induce rat hepatocytes 3D aggregation into stably-attached 3D hemispheroids."; J. Biomater. Sci. Polym. Ed. 2011 , vol. 22, No. p. 1509-1522. XP002674465; and Database Medline [Online]; US National Library of Medicine (NLM); Bethesda. MD, US; Jul. 12, 2010 (Jul. 12, 2010); Database accession No. NLM20626957 abstract.

Cherian B M et al: "Isolation of nanocellulose from pineapple leaf fibres by steam explosion"; Carbohydrate Polymer, vol. 81. No. 3. Jul. 7, 2010 (Jul. 7, 2010), pp. 720-725. XP027051121, ISSN: 0144-8617 [retrieved on May 14, 2010].

Borges A C et al: "Nanofibrillated cellulose composite hydrogel for the replacement of the nucleus pulposus", Acta Biomaterialia, vol. 7. No. 9, Sep. 1, 2011 (Sep. 1, 2011), pp. 3412-3421. XP55025311, ISSN: 1742-7061. DOI: 10.1016/j.actbio.2011.05.029.

Czaja W K et al: "The Future Prospects of Microbial Cellulose in Biomedical Applications", Biomacromolecules, vol. 8. No. 1, Jan. 1, 2007 (Jan. 1, 2007), pp. 1-12. XP55025315, ISSN: 1525-7797, DOI: 10.1021/bm060620d [retrieved on Dec. 1, 2006].

Valo H et al: "Immobilization of protein-coated drug nanoparticles in nanofibrillar cellulose matrices—Enhanced stability and release", Journal of Controlled Release, vol. 156. No. 3, Dec. 1, 2011 (Dec. 1, 2011), pp. 390-397, XP55025318, ISSN: 0168-3659. DOI: 10.1016/j.jconrel.2011.07.016 [retrieved on Jul. 23, 2011].

Pääkö M et al: "Enzymatic Hydrolysis Combined with Mechanical Shearing and High-Pressure Homogenization for Nanoscale Cellulose Fibrils and Strong Gels", Biomacromolecules, vol. 8. No. 6. Jun. 2007 (Jun. 2007). pp. 1934-1941. XP003026928, ISSN: 1525-7797. 001: 10.1021/BM061215P [retrieved on May 3, 2007].

International Search Report of PCT/FI2011/050939.

International Preliminary Report on Patentability of PCT/F12011/050939.

Deguchi, S. et al. Preparation and characterisation of nanofibrous cellulose plate as a new solid support for microbial culture. Soft Matter, 2007, vol. 3, No. 9, p. 1170-1175.

Ping, W. et al. 'Study on the feasibility of bacterial cellulose as tissue engineering scaffold', Multi-Functional Materials and Structures II, 2nd International Conference on Multi-Functional Materials and Structures, Advanced Materials Research, 2009, vols. 79-82, p. 147-150.

Recouvreux, D.O.S. et al. Novel three-dimensional cocoon-like hydrogels for soft tissue regeneration. Mater. Sci. Eng. C, Mar. 2011, vol. 31, No. 2, p. 151-157. Available online (Epub) Aug. 13, 2010.

Bäckdahl H et al: "Mechanical properties of bacterial cellulose and interactions with smooth muscle cells", Biomaterials, vol. 27. No. 9. Mar. 2006 (Mar. 2006), pp. 2141-2149. XP025097665, ISSN: 0142-9612, DOI: 10.1016/J.BIOMATERIALS.2005.10.026 [retrieved on Mar. 1, 2006].

The State Intellectual Property Office of the People's Republic of China Notice on the First Office Action for Application No. 201180062719.2 dated Apr. 11, 2014.

Cai, Z. and Jaehwan, K., "Preparation and characterization of novel bacterial cellulose/gelatin scaffold for tissue regeneration using bacterial cellulose hydrogel", Journal of Nanotechnology in Engineering and Medicine—Transactions of the ASME, vol. 1 (2010).

Degushi et al., "Nanofibrous cellulose as novel solid support for microbial culture", Polymer Preprints, Japan, 57(1):1811 (2008).

Mugishima et al., "Cultivation of Tissue Cells Using Cellulose Fibrils and Functional Analysis Therof", Fiber Preprints, 65(1) Annual Meeting (2010).

Teramoto et al., "Cell Culturing of Osteoblasts Using cellulose Nanofibers", 288 Regenerative Medicine, vol. 6. Suppl (2007).

Celish, Tiara, Website of Daicel FineChem Ltd, www.daicelfinechem.jp/business/wspdiv/celish.html, retrieved Mar. 25, 2016.

Kutcharlapati et al., "Influence of Nano Cellulose Fibres on Portland Cement Matrix," (2008), vol. 20, No. 3, pp. 307-314.

Hay et al., "Efficient differentiation of hepatocytes from human embryonic stem cells exhibiting markers recapitulating liver development in vivo", Stem Cells, (Apr. 2008), vol. 26, No. 4, pp. 894-902.

Ahola et al. "Enzymatic Hydrolysis of Native Cellulose Nanofibrls and Other Cellulose Model Films: Effect of Surface Structure," (2008), vol. 24, pp. 11592-11599.

Bodin et al., "Biomacromolecules," vol. 8, No. 12, 2007, pp. 3697-3704.

Mugishima et al. "Cultivation of Tissue Cells Using Cellulose Fibrils and Functional Analysis Therefo," vol. 65, No. 1, 2010, pp. 268, Fiber Preprints, Japan.

Deguchi et al., "Nanotibrous Cellulose as Novel Solid Support for Microbial Culture," vol. 57, No. 1, 2008, pp. 1811 Polymer Preprints, Japan.

Mueller, Bacterial Nanocellulose Would Dressing As Drug Delivery System, : Abstracts of Paper; 239th National Meeting of the American Chemical Society V. 239, 20100321, P Cell-22, American Chemical Society.

Hubbe et al., "Cellulosic Nanocomposites: A Review." BioResources 2008:3(3);929-980.

Michailova et al., "Rheological characteristics and diffusion processes in mixed cellulose hydrogel matrices." J. Drug Del. Sci. Tech 2005:15(6);443-449.

Cherian et al., "Isolation of nanocellulose from pineapple leaf fibres by steam explosion." Carbohydrate Polymers 81 (2010) 720-725.

Hoare et al., "Hydrogels in drug delivery: Progress and challenges. "Polymer 49 (2008) 1993-2007.

Svensson et al., "Bacterial cellulose as a potential scaffold for tissue engineering of cartilage" Biomaterials, Feb. 1, 2005 Elsevier Science Publishers BV., Barking, GB, vol. 26, Nr: 4, pp. 419-431.

(56) References Cited

OTHER PUBLICATIONS

Sanchavanakit et al.,"Growth of Human Keratinocytes and Fibroblasts on Bacterial Cellulose Film," Biotechnology Progress, Aug. 4, 2006 American Chemical Society, vol. 22, Nr 4, pp. 1194-1199.

Wiegand et al., "HaCaT keratinocytes in co-culture with *Staphylococcus aureus* can be protected from bacterial damage by polihexanide," Wound Repair and Regeneration, Sep. 1, 2009 Mosby, vol. 17, Nr: 5, pp. 730-738.

Grande et al., "Nanocomposites of bacterial cellulose/hydroxyapatite for biomedical applications," Acta Biomaterialia, Jun. 1, 2009 Elsevier, Amsterdam, NL, vol. 5, Nr: 5, pp. 1605-1615.

Elzinga et al., "Clinical evaluation of a PHMB-impregnated biocellulose dressing on paediatric lacerations," Journal of Wound Care, Jun. 1, 2011, vol. 20, Nr: 6, pp. 280-284.

Trovatti et al., "Biocellulose Membranes as Supports for Dermal Release of Lidocaine," Biomacromolecules, Nov. 14, 2011 American Chemical Society, vol. 12, Nr: 11, pp. 4162-4168.

Pitkanen, "Nanofibrillar cellulose—in vitro study of cytotoxic and genotoxic properties," 2010, 16 pages.

Trojani, "Three-dimensional culture and differentiation of human osteogenic cells in an injectable hydroxypropylmethycellulose hydrogel," 2005, 9 pages.

Sadek, "Suspension-mediated Induction of Hepa 1clc7 Cyp1a-1 Expression is Dependent on the Ah Receptor Signal Transduction Pathway," 1994, 5 pages.

Entcheva, "Functional cardiac cell constructs on cellulose-based scaffolding," 2004, 10 pages.

TM Broth Datasheet, Medium data, 1 page.

Ono, "Recent Progress for Cellulose Nanofiber Materials,"—R&D for the gel material and the new sheet, 2008, 6 pages.

Kondo, "New Aspects of Cellulose Nanofibers," vol. 54, No. 3, 2008, p. 107-115.

Office Action from Canadian Application No. 2,815,276 dated Sep. 11, 2017.

Office Action in Canadian Patent Application No. 2,815,276, dated Jul. 4, 2018 (5 pages).

\* cited by examiner

PLANT DERIVED CELL CULTURE MATERIAL

CLAIM FOR PRIORITY

This application claims priority under 35 USC 371 to International Application No. PCT/FI2011/050939, filed on Oct. 26, 2011, which claims priority to Finnish Patent Application No. 20106121, filed Oct. 27, 2010, each of which is hereby incorporated by reference in its entirety.

FIELD OF THE INVENTION

The invention relates to plant derived cell culture and cell delivery compositions comprising cellulose nanofibers and/or derivatives thereof.

BACKGROUND OF THE INVENTION

Health care remains at the foremost frontiers for scientific research. The need to discover and develop cost-effective and safer medications is ever increasing. The ability to accurately model the cellular organization within a particular tissue or organ is of paramount importance. A close replica of the in vivo system to in vitro would require cell growth in three dimensions (3D). The "cross-talk" achieved between the cells in a 3D cell culture in vitro is a close mimic of cell growth under physiological conditions. Indeed, 3D cell culture have assumed significance in efforts directed towards regenerative medicine, better understanding of chronic diseases and providing superior in vitro model system for screening drugs and toxicological assays. Its emergence is thus being aptly touted as "biology's new dimension".

Intense research efforts are on to identify and develop "factors and scaffolds" that would favor 3D cell growth in vitro. The cells under physiological conditions not only "cross-talk" amongst themselves but also interact with the cellular microenvironment, the extra-cellular matrix (ECM), with which they reside. The ECM provides structural support to the cells and also contributes to signaling and directing cell fate. Mostly, the ECM is composed of glycosaminoglycans and fibrous proteins such as collagen, elastin, laminin and fibronectin self assembled into nanofibrillar network. An ideal scaffold for 3D cell growth should be able to mimic the structural component of native ECM, support cell growth and maintenance, have the right sized network of interconnected pores for efficient cell migration and transfer of nutrients to the cells. In essence, the mechanical and chemical properties of the scaffold should lead to cellular function as in the native state.

Hydrogels, both of synthetic and natural origin have emerged as suitable scaffolds for 3D cell culture. The network of interconnected pores in hydrogels allows for retention of a large amount of biological fluid, facilitates transport of oxygen, nutrients and waste. Furthermore, most hydrogels can be formed under mild cytocompatible conditions and the biological properties can be modulated by surface chemistry. Engineered hydrogels with modified mechanical, chemical and biological properties have the potential to mimic the ECM and thus establish their utility in 3D cell culture. Commercial products for 3D cell culturing are for example PURAMATRIX™ (3DM Inc.) and MATRIGEL® (BD Biosciences). PURAMATRIX™ is a hydrogel of self-assembled peptide nanofibers which resembles the structure of natural fibrillar collagen in ECM with fiber diameter 5-10 nm. It has also high water content, typically 99.5%. U.S. Pat. No. 7,449,180 and WO 2004/007683 disclose peptide hydrogels. MATRIGEL® is gelatinous protein mixture secreted by mouse tumor cells. The mixture resembles the complex extracellular environment found in many tissues and is used by cell biologists as a substrate for cell culture. MAXGEL™ ECM Matrix (Sigma-Aldrich), which includes a mixture of human ECM components, forms a gel in ambient temperature.

Bacterial cellulose has been used in wound healing membranes and as a scaffold in cell culture. The limitation in the use of bacterial cellulose in cell culture is the inherent structure of the fermented material; upon cultivation, BC is formed as very tight membranes in air water interphase in the fermenter. The formed membranes are too tight for many 3D cell culturing tasks and various modifications are needed to improve the porosity, which is needed for cell penetration and formation of cell clusters.

Hydrogel materials are also widely used in other types of culturing tasks where hydrophilic supporting material is needed, for example agar type hydrocolloids are widely used in plant cell, bacterial, and fungi culturing for various microbiological purposes.

U.S. Pat. No. 5,254,471 discloses a carrier for culturing cells made of ultra fine fibers. WO 2009/126980 discloses cellulose-based hydrogel, which contains cellulose exhibiting an average degree of polymerization of 150-6200.

The solutions of the prior art have been found to be rather unsatisfactory in cell culture. All the present 2D and 3D cell culture methods and matrices require the use of animal based chemicals or compounds on the biomaterial media in order to cells to be maintained and multiplied. Maintenance of stem cells is especially demanding and there exists no simple solutions for matrix used with cell culture media which would keep the stem cells alive. The presence of animal based compounds in cell culture environment generates a serious risk of immunoreactions, and different types of toxicity issues, which finally will kill the cultured cells. Cell culture matrices containing animal-based additives are not suitable for use with stem cells, especially, if stem cells are to be used for tissue transplantation and tissue technology (engineering). Furthermore, many of the polymers proposed for use in the cell culture media do not tolerate a physiological temperature or are toxic for cells.

BRIEF DESCRIPTION OF THE INVENTION

There is a clear need for improved cell culture material that is able to provide proper three or two dimensional support for various cell types. Those functional 3D cell models can be utilized as tools in drug discovery replacing the animal experiments and being more advanced than the nowadays used 2D cell models. Transportation of cultured cells is also highly desirable, for example when tissue transfers or cell therapy is the goal. Possibility to transfer cultured cell clusters in 3D matrix is desirable when different in vitro cell models are being developed. Existing 3D cell culture biomaterials do not allow transferring the hydrogel matrix with a needle without seriously damaging the cultured cells.

An object of the present invention is thus to provide a novel approach to at least partially solve or alleviate the aforementioned problems arising in the prior art. The objects of the invention are achieved by a cell culture or cell delivery composition comprising cellulose nanofibers or a derivative thereof which is characterized by what is stated in the independent claims. The preferred embodiments are disclosed in the dependent claims.

The present invention is based on the use of cellulose nanofibers and/or derivatives thereof in 2D and 3D cell culture matrix. The present invention provides the use of cellulose nanofibers and/or derivatives thereof in the cell culture matrix. The use of cellulose nanofibers and/or derivatives thereof as 2D and 3D cell culture matrix abolishes the need to use animal based additives to multiply and achieve proliferation of cells on a matrix containing the cellulose nanofibers and/or derivatives thereof.

The present inventor surprisingly found out that the plant derived CNF hydrogel can be used without any modifications as biomimetic human ECM for 3D cell culture. Cell proliferation and viability data suggests CNF hydrogel to be an optimal biomaterial for 3D cell scaffolds for advances functional cell based high throughput screening assays in drug development, in drug toxicity testing and in regenerative medicine and further for cell delivery in vivo.

The present inventors describe for the first time the physical and biocompatibility properties of plant derived CNF hydrogel. Plant cellulose is extensively used in the paper and textile industry and is abundant naturally. The native cellulose nanofiber hydrogel is opaque. Chemical modification of cellulose pulp prior to mechanical disintegration gives rise to optically transparent hydrogels.

The present invention is based on experimental studies on hydrogels composed of cellulose nanofibers (CNF), which are dispersed in aqueous environment. The nanofibers are highly hydrophilic due to hydroxyl functionalities of cellulose polymers and partly covered with hemicellulose polysaccharides.

Accordingly the present invention provides as a first aspect a cell culture or cell delivery composition comprising cellulose nanofibers or a derivative thereof, wherein the cellulose nanofiber in a form of a hydrogel or membrane.

A significant advantage of the present invention is that cells can be maintained (and proliferated) on or in the biomaterial media without animal or human based chemicals originating outside the cells. The cells are evenly dispersed on or in the media/matrix containing cellulose nanofibers or a derivative thereof. Cells divide on or in the media, start to proliferate and the cell clusters start to grow spontaneously without the accumulation of cells on the bottom of the cell culture platform. The homogenous dividing of the cells in the cellulose nanofibers or a derivative thereof is a prerequisite for the biomaterial to function as 3D cell culture media.

Further advantages of the present invention include: cellulose nanofibers and/or derivatives thereof are inert and give no fluorescent background. The media comprising cellulose nanofibers or a derivative thereof can be injected. Injectability is explained by the rheological properties. The injection can be performed so that the cells stay stable inside matrix and they are homogeneously distributed in the matrix after injection.

DETAILED DESCRIPTION OF THE INVENTION

Figure 1:
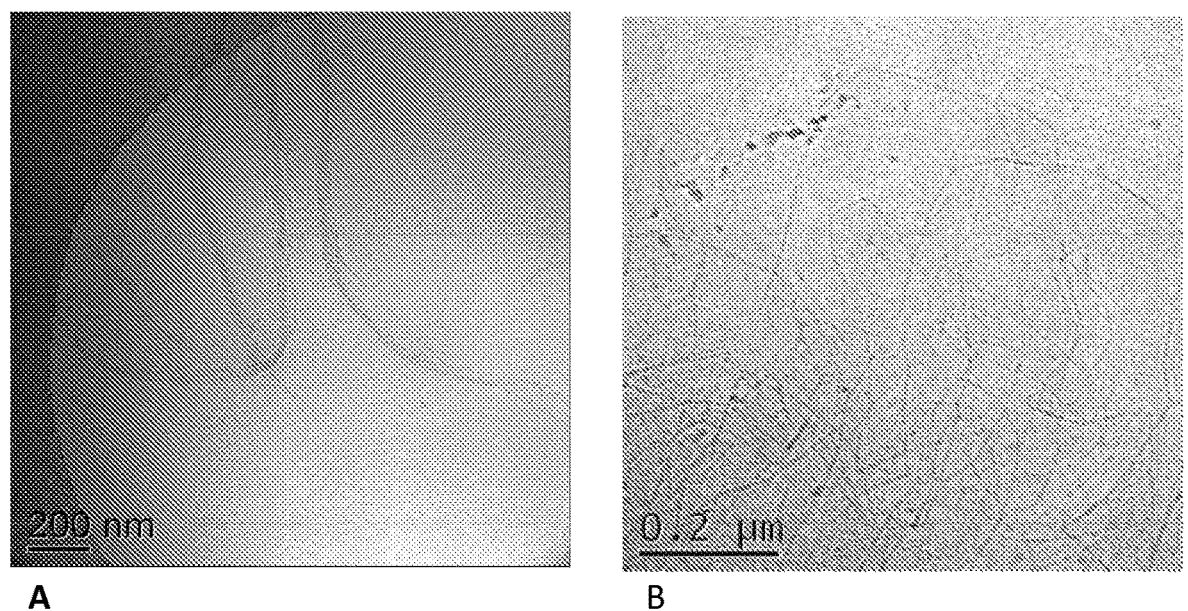
FIG. 1 depicts cryo-TEM images of cellulose nanofiber hydrogels. Native CNF is on the left side (A) and transparent CNF is on the right side (B).

The present invention relates to a cell culture or delivery composition comprising cellulose nanofibers and/or derivatives thereof, wherein the cellulose nanofibers or derivatives thereof are in a form of a hydrogel or membrane. Cellulose nanofibers or derivatives thereof can be obtained from non-animal based material such as raw material comprising plant material.

Unless otherwise specified, the terms, which are used in the specification and claims, have the meanings commonly used in the cell culture. Specifically, the following terms have the meanings indicated below.

The term "cell culture or delivery composition" refers to a material comprising cellulose nanofibers or derivatives of cellulose nanofibers and which material is used as a cell culture medium or for cell delivery. Said composition can also be used to transfer cells or cell clusters. Cellulose nanofibers can be in a form or a hydrogel or membrane. Said composition may further contain various additives such as special extra cellular matrix components, serum, growth factors, and proteins.

The term "cellulose raw material" refers to any cellulose raw material source that can be used in production of cellulose pulp, refined pulp, or cellulose nanofibers. The raw material can be based on any plant material that contains cellulose. Plant material may be wood. Wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed.

The term "cellulose pulp" refers to cellulose fibers, which are isolated from any cellulose raw material using chemical, mechanical, thermo mechanical, or chemi thermo mechanical pulping processes. Typically the diameter of the fibers varies between 15-25 µm and length exceeds 500 µm, but the present invention is not intended to be limited to these parameters.

Cellulose in the present invention is structurally type I cellulose.

The term "cellulose nanofiber" refers to a collection of isolated cellulose nanofibers (CNF) or nanofiber bundles derived from cellulose raw material or cellulose pulp. Nanofibers have typically high aspect ratio: the length might exceed one micrometer while the number-average diameter is typically below 200 nm. The diameter of nanofiber bundles can also be larger but generally less than 1 µm. The smallest nanofibers are similar to so called elementary fibrils, which are typically 2-12 nm in diameter. The dimensions of the fibrils or fibril bundles are dependent on raw material and disintegration method. The cellulose nanofibers may also contain some hemicelluloses; the amount is dependent on the plant source.

Mechanical disintegration of cellulose nanofibers from cellulose raw material, cellulose pulp, or refined pulp is carried out with suitable equipment such as a refiner, grinder, homogenizer, colloider, friction grinder, ultrasound sonicator, fluidizer such as microfluidizer, macrofluidizer or fluidizer-type homogenizer. Preferably the "cellulose nanofibers" is mechanically disintegrated material.

"Cellulose nanofibers" or "cellulose nanofibers and/or derivatives thereof" can also be any chemically or physically modified derivate of cellulose nanofibers or nanofiber bundles. The chemical modification can be based for example on carboxymethylation, oxidation, such as TEMPO-oxidation, esterification, or etherification reaction of cellulose molecules. Modification can also be realized by physical adsorption of anionic, cationic, or non-ionic substances or any combination of these on cellulose surface. The described modification can be carried out before, after, or during the production of cellulose nanofibers. Certain modifications may lead to CNF materials that are degradable in human body.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. This pretreatment provides the "cellulose nanofibers" excellent gelling properties and transparency. This pretreated product is referred to as acid-base pretreated or ion exchanged "cellulose nanofibers".

Microbial purity of the "cellulose nanofibers" is essential for the cell culture performance. Therefore, the "cellulose nanofibers" are sterilized prior to cell culture experiments in a hydrogel or membrane form. In addition to that it is important to minimize the microbial contamination of the product before and during the fibrillation. Prior to fibrillation, it is advantageous to aseptically collect the cellulose pulp from the pulp mill immediately after bleaching stage when the pulp is still sterile.

There are several widely used synonyms for cellulose nanofibers. For example: nanocellulose, nanofibrillated cellulose (CNF), nanofibrillar cellulose, cellulose nanofiber, nano-scale fibrillated cellulose, microfibrillar cellulose, microfibrillated cellulose (CNF), or cellulose microfibrils. Cellulose nanofibers produced by certain microbes has various synonymes, such as bacterial cellulose, microbial cellulose (MC), biocellulose, nata de coco (NDC), or coco de nata.

Cellulose nanofibers described in this invention is not the same material as so called cellulose whiskers, which are also known as: cellulose nanowhiskers, cellulose nanocrystals, cellulose nanorods, rod-like cellulose microcrystals or cellulose nanowires. In some cases, similar terminology is used for both materials, for example by Kuthcarlapati et al. (Metals Materials and Processes 20(3):307-314, 2008) where the studied material was called "cellulose nanofiber" although they clearly referred to cellulose nanowhiskers. Typically these materials do not have amorphous segments along the fibrillar structure as cellulose nanofibers, which lead to more rigid structure. Cellulose whiskers are also shorter than cellulose nanofibers; typically the length is less than one micrometer.

The dimensions of individual cellulose nanofibers are quite close to aforementioned dimensions of collagen fibers in ECM, i.e. 4-10 nm. Therefore, CNF based hydrogels can be used as 3D cell culture matrix.

In the cell culture experiments of the present invention, two kinds of cellulose nanofibers were used: opaque native CNF and optically transparent CNF, which was TEMPO-oxidized cellulose. Detailed description of the materials is presented in the Examples, Materials and methods section.

The term "cellulose nanofiber hydrogel" refers to aqueous dispersion of cellulose nanofibers.

The term "cellulose nanofiber membrane" refers to wet or dry sheet-like formation of cellulose fibers. The membranes are typically produced by filtration of dilute cellulose nanofiber dispersion with vacuum filtration apparatus with a proper filter. Solvent casting may also be used to obtain aforementioned membrane structures. The obtained membrane can be used as such in wet state or dried prior use.

The cellulose nanofibers or a derivative thereof of the present invention can comprise chemically or physically modified derivates of a cellulose nanofibers or nanofiber bundles.

The cell culture or drug delivery composition of the present invention may further comprise suitable additives selected from the group consisting of special extra cellular matrix components, serum, growth factors, and proteins.

The present invention also relates to a cell culture or cell delivery matrix, wherein the matrix comprises living cells and the cell culture or cell delivery composition forming a hydrogel and wherein the cells are present in the matrix in a three-dimensional or two-dimensional arrangement.

Cells can be any cells. Any eukaryotic cell, such as animal cells, plant cells and fungal cells are within the scope of the present invention as well as prokaryotic cells such as bacterial cells.

Depending on the cell line, the experiments are carried out on 2D or 3D, i.e. the cells are cultivated on the CNF membranes or gels or the cells are dispersed homogeneously in the CNF hydrogels or CNF membranes. The specific examples of the present invention disclose that spontaneously arising retina pigment epithelial (ARPE-19) cells form monolayer, whereas human hepatocellular carcinoma (HepG2) cells produce either monolayer or cell colonies.

Cells may be detected using any known detection means or dye known in the art.

The present invention also relates to a method for producing a composition according to any of the preceding claims, comprising the steps of providing cellulose nanofibers and/or derivatives thereof; optionally mixing together said cellulose nanofibers and/or derivatives thereof with water; and transferring or placing the cellulose nanofibers and/or derivatives thereof or the obtained mixture to the suitable environment for cell culture or delivery.

Cellulose nanofiber hydrogels or membranes or derivatives thereof or the composition of the present invention can be used as a cell delivery material.

Cellulose nanofibers hydrogels or membranes or derivatives thereof or the cell culture or cell delivery composition can be used for delivering material for clinical use.

The present invention relates to a microbiological use of cellulose nanofibers or a derivative thereof or the composition according the present invention for laboratory and/or industrial purposes as a medium or a compound of a media for maintaining cells in vitro.

The composition comprising cellulose nanofibers or derivatives thereof can be used for immobilizing cells or enzymes.

The present invention also relates to a method of culturing cells, wherein the method comprises the steps of providing cells; contacting the cells with a cell culture composition comprising cellulose nanofibers or a derivative thereof to form a matrix; and culturing the cells within said matrix in a three-dimensional or two-dimensional arrangement.

The present invention further relates to a composition, method or use, wherein the cells are eukaryotic cells.

The present invention further relates to a composition, method or use, wherein the cells are prokaryotic cells. Prokaryotic cells comprise micro-organisms such as aerobic or anaerobic bacteria, viruses, or fungi such as yeast and molds.

The present invention further provides a composition, method or use, wherein the cells are stem cells.

The removal of cellulose nanofibers can be carried out for example with enzymes using enzymatic degradation of cellulose molecules. Proper enzymes are for example commercially available cellulases. The cultured cell lines can be also genetically engineered to produce the needed enzyme protein into the culture system.

The present invention also relates to a method for removing cellulose nanofibers or a derivative thereof from the cell growth or cell culture material, the method comprising the steps of providing material comprising cell growth medium and cells and optionally a medicament; diluting said material with aqueous or non-aqueous liquid; and removing the cellulose nanofibers by decantation. Moderate centrifugation can be used to sediment the cells and cell aggregates prior to decantation.

The present inventors surprisingly found out that the plant derived CNF hydrogel can be used even without any modifications as biomimetic human ECM for 3D cell culture. Cell proliferation and viability data suggests CNF hydrogel to be an optimal biomaterial for 3D cell scaffolds for advanced functional cell based high throughput screening assays in drug development, in drug toxicity testing and in regenerative medicine and further in cell delivery in vivo.

The present invention discloses for the first time the physical and biocompatibility properties of plant derived CNF hydrogel. Plant cellulose is extensively used in the paper and textile industry and is abundant naturally. The native cellulose nanofiber hydrogel is opaque. Chemical modification of cellulose pulp prior to mechanical disintegration gives rise to optically transparent hydrogels.

Cellulose nanofibers of the present invention can be used in the form of hydrogel or dry or wet membrane. The gel strength of CNF hydrogel can be easily altered by dilution. Cellulose nanofibers or a derivative thereof having similar properties is not toxic to cells.

If cellulose nanofiber hydrogels are compared to UV cross-linkable cell culture hydrogels, like hyaluronic acid or PEG hydrogels, the CNF materials are considered much less toxic. In UV cross-linkable gels harmful photoinitiators are needed to initiate gelation while the CNF hydrogels are formed spontaneously. The non-covalent nature of the CNF hydrogels allows also adjustment of the porosity by dilution.

Cells are evenly spread in the cellulose nanofiber hydrogels and can automatically start to duplicate and grow into 3D cell clusters without sedimentation to the bottom of the cell culture platform. All the presently used commercial 3D cell culture media require the addition of adhesion peptide so that the cells would form 3D structure on the cell culture platform.

Cellulose nanofibers according to the present invention or a derivative thereof can be used without adhesion peptide. Cells attach to the platform and spontaneously distribute homogenously into the cellulose nanofiber hydrogel. Cells are suspended homogenously into the continuous phase due to mechanical support provided by the cellulose nanofibers fibers. The remarkably high yield stress stabilizes the cells and the grown cell clusters against sedimentation.

Plant origin cellulose nanofiber hydrogels function without adhesion peptide and/or tailor-made porosity, whereas bacterial cellulose nanofibers require adhesion peptide. Bacterial cellulose has been used directly after fermentation, in which case the resulting membrane structure is considerably firmer than the hydrogel of the present invention i.e. a hydrogel from cellulose nanofibers. Therefore prior art methods have required additional processes for making the hydrogel matrix more porous.

The firmness of the cell culture media containing cellulose nanofibers in gel form can be adjusted without influencing the properties of the cell culture. Cellulose nanofibers originating from bacteria are also thicker than cellulose nanofibers from other sources and therefore not freely modifiable for the cell culture.

Cells grow in the 3D matrix or on the matrix. Said material may be injectable or sheet-like membrane with appropriate surface topology.

The properties of CNF are close to optimal for 3D cell culturing: transparent, non-toxic, highly viscous, high suspending power, high water retention, good mechanical adhesion, non-animal based, resembles ECM dimensions, insensitive to salts, temperature or pH, not degradable, no autofluorescence. CNF has negligible fluorescence background due to the chemical structure of the material. Furthermore, CNF gel is not toxic to the cells.

Cells can be cultured or grown on CNF gels for long time, for example 2 to 7 days or even longer time. Cells can be also cultured or only suspended in the hydrogel for a short time, for example minutes to several hours. Cells use nanocellulose fiber matrix as growing scaffold/support used as platform. Cells form clusters thus indicating the usefulness of cellulose nanofibers as 3D cell culture scaffold. Cells grow as layers or cell aggregates on or within the CNF gel, depending on the deposition method and the cell type.

The non-toxic CNF hydrogel is equally good ECM for the studied cells as the human ECM based MAXGEL™. Viability of cells is even higher than in PURAMATRIX™ or HYDROMATRIX™. Neither human nor animal based ECM components are added to CNF hydrogels. Addition of fibronectin or collagen IV into CNF based systems can be beneficial in some cases, however. Based on the diffusion studies the CNF hydrogel is highly permeable and is freely facilitating the exchange of oxygen, nutrients and water soluble metabolites of the cells.

Cryo transmission electron microscopy shows that the CNF hydrogel is composed of a mixture of individual cellulose nanofibrils and fiber bundles. The dimensions of CNF are alike native human collagen, which is a natural ECM component and commonly used as a cell support. The strength (elasticity) of CNF hydrogel stays nearly constant as function of used frequency from 0.01 to 1 Hz. Rheology data reveals the shear viscosity of about several hundred kilo Pascals in rest (low shear stress) to drop to few Pascals within one Pascal shear stress. That behavior is rather unique for biomaterial hydrogels. It enables the extremely good suspending capacity and support of cells and by the shear-thinning behaviour enables the desired easy dispensing and injection of cells in CNF hydrogel independently of the size of the used needles, whose behaviors are not obtained earlier for other cell culture biomaterial hydrogels. The mechanical properties of elasticity and stiffness are optimal for CNF hydrogels for the 3D cell culture growth and injection of cells.

The advantage of the present invention is that the dimensions of the fibrillar network of cellulose nanofibers or a derivative thereof is very close to natural ECM network of collagen nanofibers. Furthermore, cellulose nanofibers or a derivative thereof is non-animal based material, i.e. there is no risk for disease transfer. Currently, most of the commercial products are isolated from animals. Further, the invention provides possibilities to adjust physical form as CNF materials from hydrogels to membranes can be utilized.

Injectable hydrogel forms supporting matrix around the cells due to very high yield stress. CNF membranes are transparent and highly porous. Mass production is easy compared to alternatives.

Native cellulose nanofibers are not toxic to the cells. The cell proliferation is almost double in case of cellulose nanofibers or a derivative thereof compared to the control (cells only). Cells can be controlled on CNF hydrogels for long time (for example for 2-7 days). Cells use cellulose nanofiber matrix as a growing platform. Cells form clusters, which indicate the usefulness of cellulose nanofibers or a derivative thereof as 3D cell culture scaffold. Cells grow as layers within the CNF gel. Cellulose nanofibers or a derivative thereof have negligible fluorescence background. Cellulose nanofiber hydrogel has optimal elasticity, stiffness, shear stress, mechanical adhesion and porocity to be used as 3D and 2D cell culture matrix.

In aqueous environment, cellulose nanofibers form a continuous hydrogel network of dispersed nanofibers or nanofiber bundles. The gel is formed by highly hydrated fibrils that are entangled between each other, even at very low concentrations. The fibrils may interact also via hydrogen bonds. The macroscopic structure is easily destroyed with mechanical agitation, i.e. the gel starts to flow at elevated shear stress. Cellulose nanofiber hydrogels and/or derivatives thereof have not been previously described to be used as cell culture material.

Applications of the present invention include providing cell culture material for biotechnology research. Cell growth or cell culture media containing CNF may be used for maintaining and growing cells as well as for transferring cells. The present invention provides cell culture medium which can be utilized for example in tissue engineering and wound heeling. Other applications include for example drug dosage applications, biotechnological or biological medicines and their dosage as well as functional cell testing assays of 3D drugs. The unique rheological properties of the CNF hydrogel enables several applications which are based on the injectability of the hydrogel, like injection of cells or drugs in CNF hydrogel in intraocular, intramuscular, or subcutaneous treatments.

The following examples are given to further illustrate the invention and are not intended to limit the scope thereof. Based on the description, a person skilled in the art will be able to modify the invention in many ways.

EXAMPLES

Materials And Methods
Preparation of CNF Hydrogels

The opaque native CNF hydrogel (1.7 wt %) was obtained by high pressure homogenization of wet cellulose pulp fibers. Thus, the direct product from the process is a dilute cellulose nanofiber hydrogel. The transparent CNF hydrogel (0.9 wt %) was obtained by similar homogenization process of a chemically modified cellulose pulp (TEMPO-oxidized cellulose pulp). The samples were autoclave sterilized. For the cell studies, the CNF hydrogel was diluted to proper concentration and homogenized with mechanical mixing or sonication. Cryo-TEM images of native CNF and transparent CNF are presented in FIG. 1. Native, cellulose nanofiber hydrogel is composed of a mixture of individual cellulose nanofibrils and fiber bundles (FIG. 1A). The diameter of smallest fibers is approximately 7 nm, majority of the cellulose material is forming 50-100 nm in bundled structures, however. The exact length scale can not estimated from the images due to entangled and bundled nature of the material, but it seems clear that individual nanofibers are several micrometers long. The cryo-TEM image of the optically transparent CNF hydrogel shows homogeneously distributed individual cellulose nanofiber network. The diameter of these nanofibers is approximately 7 nm and the length exceeds a micrometer. The nanofibers have 100-200 nm long straight segments followed by sharp kinks along the fiber axel. These straight segments are composed of highly crystalline cellulose domains—the bending sites are formed by the amorphous parts.

Preparation of CNF Membranes

CNF membranes were prepared by vacuum filtration of an aqueous 0.2 wt % native CNF dispersion. After filtration, the wet membranes were dried under weight in oven at 55° C. for 48 h. The dry films were smooth and opaque with the grammage of 70-80 g/m$^2$.

Enzymatic Hydrolysis

Enzymatic degradation of CNF hydrogels was demonstrated by hydrolyzing gravel containing 0.5% hydrogels with Celluclast 1.5 LFG, CCN0367 (Novozymes, pHopt 5), Prot. 90 mg/ml. Degradation of native CNF was conducted at pH 5 at 50° C. for 4 days and degradation of transparent CNF at pH 7 at 21° C. for one hour. Enzyme dosage was 5 mg of enzyme to one gram of CNF.

HepG2 Cells

Origin of the HepG2 Cells

Human hepatocellular carcinoma (HepG2) cells were obtained from American Type Culture Collection (ATCC, Manassas, Va., USA).

Maintenance Culture of the HepG2 Cells

HepG2 cells were maintained in Dulbecco's modified Eagle's medium (DMEM, Gibco) supplemented with 10% fetal bovine serum, penicillin/streptomycin (Gibco), 2 mM L-glutamine (Gibco), 100 mM sodium Pyruvate (Gibco). The cells were maintained in 75 cm$^2$ culture flasks at 37° C. in an incubator with 95% RT humidity in a 5% $CO_2$ atmosphere. Cells were passaged 1:10 by trypsinization twice a week with a 1:4 split ratio. The medium was changed every 48 h and cells were subcultured at 90% confluency.

3D Culture of HepG2 Cells on CNF Hydrogel

Cellulose nanofiber hydrogel was placed in the bottom of a 96 well tissue culture plate and HepG2 cell suspension in growth media containing 25,000-50,000 cells per well were seeded either on top of the CNF hydrogel or mixed with it. CNF hydrogel concentration ranges from 0.01% to 1%.

ARPE-19 Cells

Origin of the ARPE-19 Cells

Spontaneously arising retina pigment epithelial (ARPE-19) cells were obtained from American Type Culture Collection (ATCC, Manassas, Va., USA).

Maintenance Culture of the ARPE-19 Cells

ARPE-19 cells were cultured in Dulbecco's modified Eagle's medium (DMEM): Nutrient Mixture F12, 1:1 mixture supplemented with 10% fetal bovine serum (FBS), 2 mM L-glutamine, 100 U/ml penicillin and 100 U/ml streptomycin. The cells were cultured at 37° C. in 7% $CO_2$ atmosphere. Growth medium was changed every 2-3 days and cultures were used at passage 24-30.

Culture of ARPE-19 Cells on CNF Membrane

Cellulose nanofiber hydrogel was placed in the bottom of a 96 well tissue culture plate and ARPE-19 cell suspension in growth media containing 25,000-50,000 cells per well were seeded either on top of the hydrogel or mixed with it. Hydrogel concentration ranges from 0.01% to 1%.

Human ES Cell-Derived Hepatic Progenitor Cells

Maintenance Culture of Human Embryonic Stem Cells

Human embryonic stem (hES) cell line H9 (Wisconsin International Stem Cell Bank, the "WISC Bank" do WiCell research Institute, Madison, Wis., USA) was used for the present studies. H9 cells were routinely cultured on MATRIGEL®-coated tissue culture plates in mTeSR1 medium and passaged by using 1 mg/ml Dispase (StemCell Technologies). In this condition, stem cells form 2-dimensional (2D) monolayer colonies.

3D Culture of hES Cells in CNF

H9 cell colonies were mixed with either 0.3% native CNF or 0.3% transparent CNF and cultured in mTeSR1 medium. hES cells in CNF form 3D cell clumps. In some experiments, 0.3% CNF was mixed with 58 µg/ml human fibronectin (Sigma-Aldrich).

3D Culture of Hepatic Progenitors Derived from H9 Cells in CNF

H9 cells were differentiated into hepatic progenitor cells for 11 days following the published protocol [Hay D C, Zhao D, Fletcher J, Hewitt Z A, McLean D, Urruticoechea-Uriguen A, Black J R, Elcombe C, Ross J A, Wolf R, Cui W. Efficient differentiation of hepatocytes from human embryonic stem cells exhibiting markers recapitulating liver development in vivo. Stem Cells. 2008 April; 26(4):894-902)]. The derived hepatic progenitor cells were cultured in 3D environment using either 0.3% native CNF or 0.3% transparent CNF for 7 days. In some experiments, 0.3% CNF was mixed with 13 µg/ml mouse collagen type IV (Sigma-Aldrich).

Live/Dead Staining

H9 cell clumps and hepatic progenitors in CNF were co-stained with CELLTRACKER™ Blue CMAC (Molecular Probes, Inc.) (20 µM) for live cells and propidium iodide (25 µg/ml) for dead cells. Images of the cells were acquired by confocal laser scanning microscopy (Leica TCS SP5 MP SMD FILM) at 405 nm excitation wavelength for CELLTRACKER™ Blue CMAC and 514 nm for propidium iodide.

AlamarBlue Assay for Cell Viability/Proliferation

Cell viability was quantified by AlamarBlue™ Cell Viability Assay Kit (Biotium Inc., Hayward, Calif., USA). Cellulose nanofiber hydrogel was placed in the bottom of a 96 well tissue culture plate and HepG2/ARPE-19 cell suspension in growth media containing 25,000-50,000 cells per well were seeded either on top of the hydrogel or mixed with it. Hydrogel concentration ranges from 1 to 0.01%. Cell viability and proliferation was measured as a function of days after culturing the cells on the cellulose nanofiber hydrogel in an incubator at 37° C. in 5% $CO_2$ and 95% relative humidity.

After 48 hours, AlamarBlue was added directly into culture media in 96 well plates at a final concentration of 10%. Plates were incubated for 5 h and were exposed to an excitation wavelength of 530 nm, and the emission at 590 nm to measure the fluorescence. The percent viability was expressed as fluorescence counts in the presence of CNF hydrogel as a percentage of that in the absence of cellulose nanofiber hydrogel (cells growing on plastic surface).

Background fluorescence measurements (negative control) were determined from wells containing hydrogel and dye reagent in culture medium but no cells. The mean and standard deviation for all fluorescence measurements were calculated and subsequently corrected for background and expressed as relative fluorescence.

Confocal Laser Microscopy

The viability of HepG2 cells cultured on hydrogel and the formation of 3D HepG2 spheroids were assessed with Live/Dead® Viability/Cytotoxicity Assay Kit (Invitrogen) consisting of calcein AM and ethidium homodimer.

Briefly, HepG2 cells were suspended in 1% native and transparent CNF hydrogel with or without fibronecin. The cell suspension in hydrogel was transferred to each well with cells. Cell culture media was added to each well. The hydrogel encapsulated HepG2 cells cultured for 5 days and the medium was refreshed every 48 h. After 5 days, media was removed from the wells and the encapsulated cells were washed with PBS and incubated in 'Live/Dead' solution containing 0.2 µM calcein AM and 1.0 µM ethidium homodimer for about 45 min at room temperature. Live cells were imaged using a confocal laser scanning microscope (CLSM, Leica SP2 inverted microscope, Zurich, Switzerland) equipped with argon laser (488 nm/35 mW), HC PL APO 10×/0.4 CS and HC PL APO 20×/0.7 CS (air) objectives, incubator box with air heater system (Life Imaging/Services, Switzerland), and $CO_2$ mixer (Okolab). Images were acquired from two detectors (one for Calcein and other for Ethidium homodimer). Images were created and edited with Imaris 7.0 (Bitplane). No deconvolution was done.

Example 1

Comparison of Cell Viability of HepG2 Cells in Different Cell Culture Materials

Cellulose nanofiber hydrogels were placed in the bottom of a 96 well tissue culture plate and HepG2 cell suspension in maintenance growth media containing 25,000-50,000 cells per well were seeded either on top of the hydrogel or mixed with it. Hydrogel concentration ranges from 1-0.01%. The fluorescence intensity which indicates the cell viability and proliferation was measured as a function of days after culturing the cells on the cellulose nanofiber hydrogel in an incubator at 37 C in 5% $CO_2$ and 95% relative humidity.

Three commercially available cell culture materials were used as reference 3D culture materials: MAXGEL™ (Sigma-Aldrich), HYDROMATRIX™ (Sigma-Aldrich) and PURAMATRIX™ (3DM Inc.). The experimental setup was identical for all the studied materials.

Viability of HepG2 cells was quantified by AlamarBlue™ Cell Viability Assay Kit (Biotium Inc., Hayward, Calif., USA) as presented above in the Materials and methods, Alamar Blue assay for cell viability/proliferation.

Figure 2:
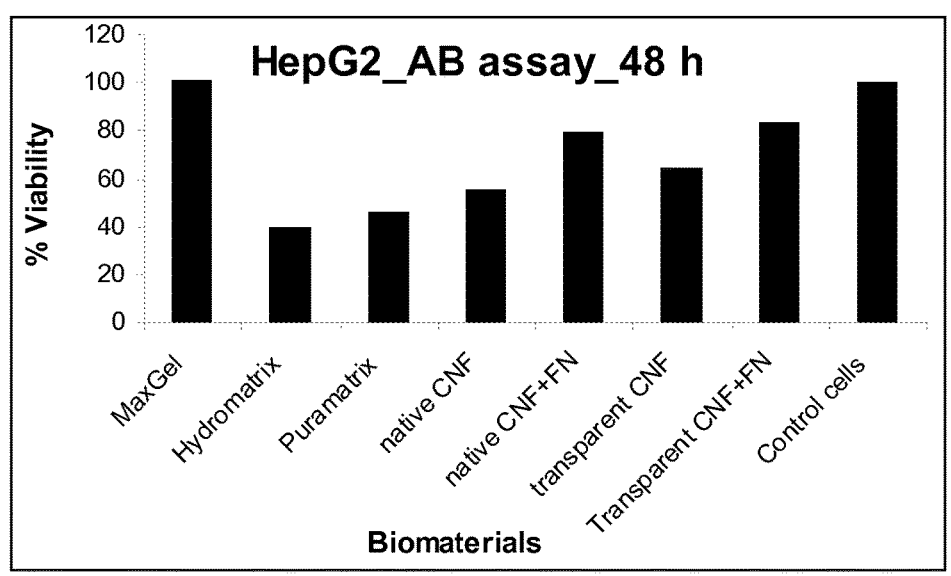
FIG. 2 depicts viability of HepG2 cells in commercial cell culture materials [MAXGEL™ (Sigma-Aldrich), HYDROMATRIX™ (Sigma-Aldrich) and PURAMATRIX™ (3DM Inc.)], in two different cellulose nanofiber materials (native CNF and transparent CNF) and in CNF in which fibronectin (FN) was added. In proliferation AB assay, cells were cultured for 48 h and the control cells were cultured in equal conditions on a plastic surface.

The viability percent of HepG2 cells for the studied materials is presented in FIG. 2. Both types of cellulose nanofiber hydrogels, i.e. native and transparent CNF show higher viability values than commercial HYDROMATRIX™ or PURAMATRIX™ reference materials. If fibronectin is added into CNF hydrogels, the viability is close to commercial MAXGEL™. In addition the proliferation and cell viability increases linearly as a function of the cell concentration in both hydrogels. This observation supports the hypothesis that hydrogel mimics human ECM components. It has all the key composition of ECM.

Example 2

Transferring of ARPE-19 Cells with a Syringe Needle

Figure 3:
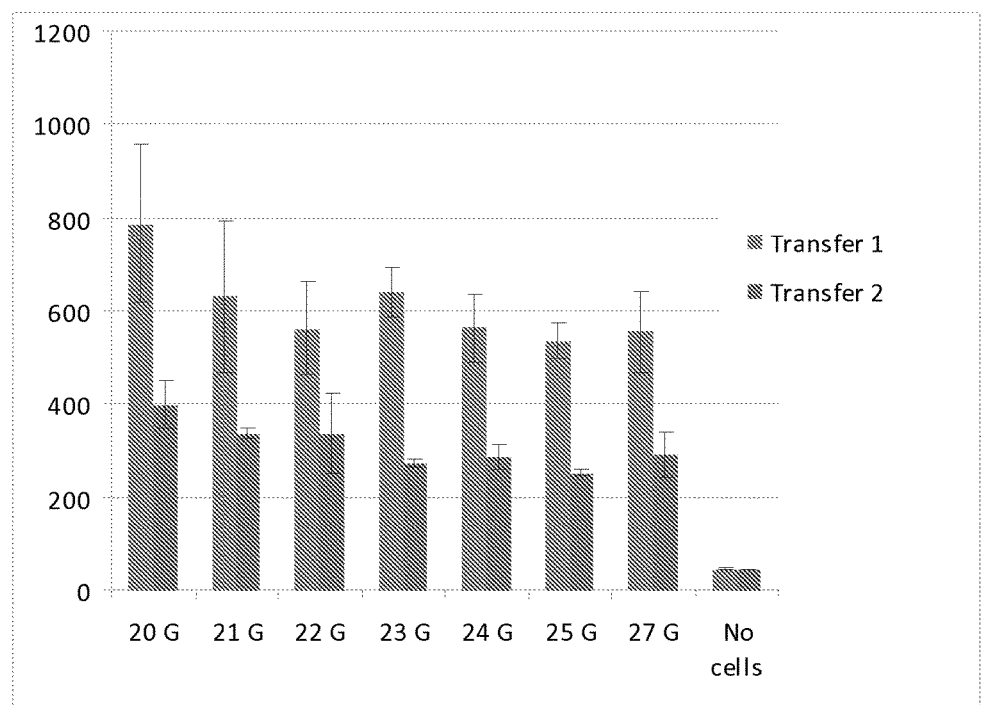
FIG. 3 depicts viability of ARPE-19 cells cultured in native CNF hydrogel after transferring the cells with a syringe needle of different sizes. The viability is presented as relative fluorescence intensity.

ARPE-19 cells (25 000 cells per well) were seeded and cultured in CNF matrix on the bottom of the 96 well plate. Viability of ARPE-19 cells after transferring the cells with a syringe needle of different sizes is presented in FIG. 3. The same phenomenon can be obtained also with other cell types like HepG2 and ES cells.

More detailed explanation of the Transferring of ARPE-19 cells with a syringe needle are follows: At the Transfer 1 in FIG. 3 the cells were incubated for 48 hours with 1.66% CNF, and after that the cells were transferred with a syringe (20 G-27 G) about 100 µl into a 96-well plate. After the transfer with the syringe the cells were incubated for 24 hours, and the viability of the cells in CNF was measured.

At the Transfer 2, the cells incubated for 24 hours in 1.66% CNF were transferred with a 27 G syringe (about 2 ml) into a fresh medium. The cells were incubated for 24 hours after the transfer, after which the cells were again transferred with a syringe (20 G-27 G) about 100 µl into 96-well plate, incubated again for 24 hours and the viability of the double transferred cells in 1.66% CNF were measured.

These experiments prove that it is possible to transfer the cells in CNF hydrogel, the transfer process was successful and the cells were alive and stayed alive during the transferring with a syringe. That phenomenon was obtained even with the smallest needle size of 27 G, and no cut off concerning the size of the needle used in the transferring process was obtained. Samples which were transferred two times (Transfer 2) showed lower proliferation rates most probably due to the 24 hours shorter incubation time at the beginning of the experiment. Transfer of cells in CNF hydrogel proves that the cells were indeed within the hydrogel and stayed there since cells which are attached to the plate will not be transferred (no trypsination). These experiments showed that the cells remained viable during the transfer.

Example 3

Stem Cells

Live/Dead Staining of hES Cell-Derived Hepatic Progenitor Cells

Figure 15:
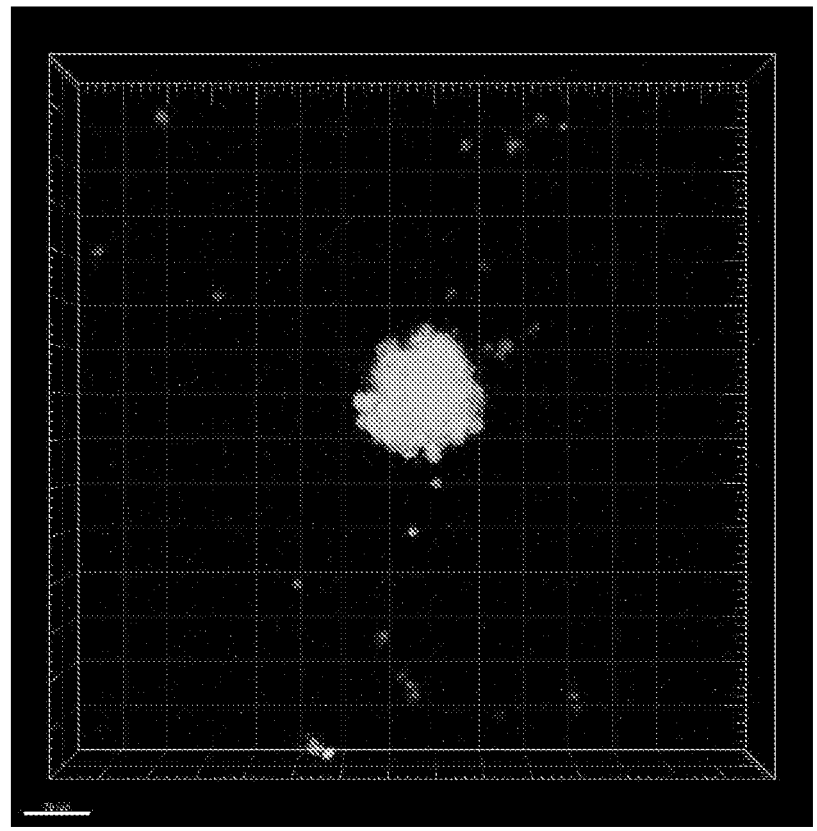
FIG. 15 depicts confocal microscopy image of human ES cell derived hepatic progenitor cells, which are imbedded in native CNF hydrogel. Scale bar: 70 μm.

Human ES cell-derived hepatic progenitor cells were imbedded in native CNF hydrogel (FIG. 15) and cultured for 7 days with and without collagen IV. No background was detected. Human ES cell-derived hepatic progenitor cells were imbedded in transparent CNF hydrogel and cultured for 7 days with and without collagen IV. No background was detected, which makes this material extremely easy to use in this context. Usually other materials used e.g. MATRIGEL® and MAXGEL™ have a significant fluorescent background, and therefore it is difficult to work with those matrices. The ES cells are possible to keep in CNF hydrogel, they survive and thus this material is able to keep them alive. In addition, ES cells form also 3D structure, which has not been observed earlier with any other material.

Example 4

Diffusion of Dextrans Through CNF Hydrogels

Detailed knowledge on the diffusion properties of a cell culture material is important. The cell culture material should be porous enough to allow diffusion of nutrients and oxygen to the cultured cells as well as to enable efficient diffusion of metabolites from the cells. The diffusion properties of CNF hydrogel was demonstrated with different molecular weight dextrans in the following manner:

400 µl of transparent or opaque CNF (1%) was planted per filter on the apical compartment in Transwell™ filter well plates (filter pore size 0.4 µm). 1 ml of PBS was added into the basolateral side and 100 µl (25 µg) of fluorescent labeled dextrans were added on top of the hydrogels (MW of 20 k, 70 k and 250 k). Plate was fixed firmly and left undisturbed on a well plate rocker. 100 µl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Figure 4:
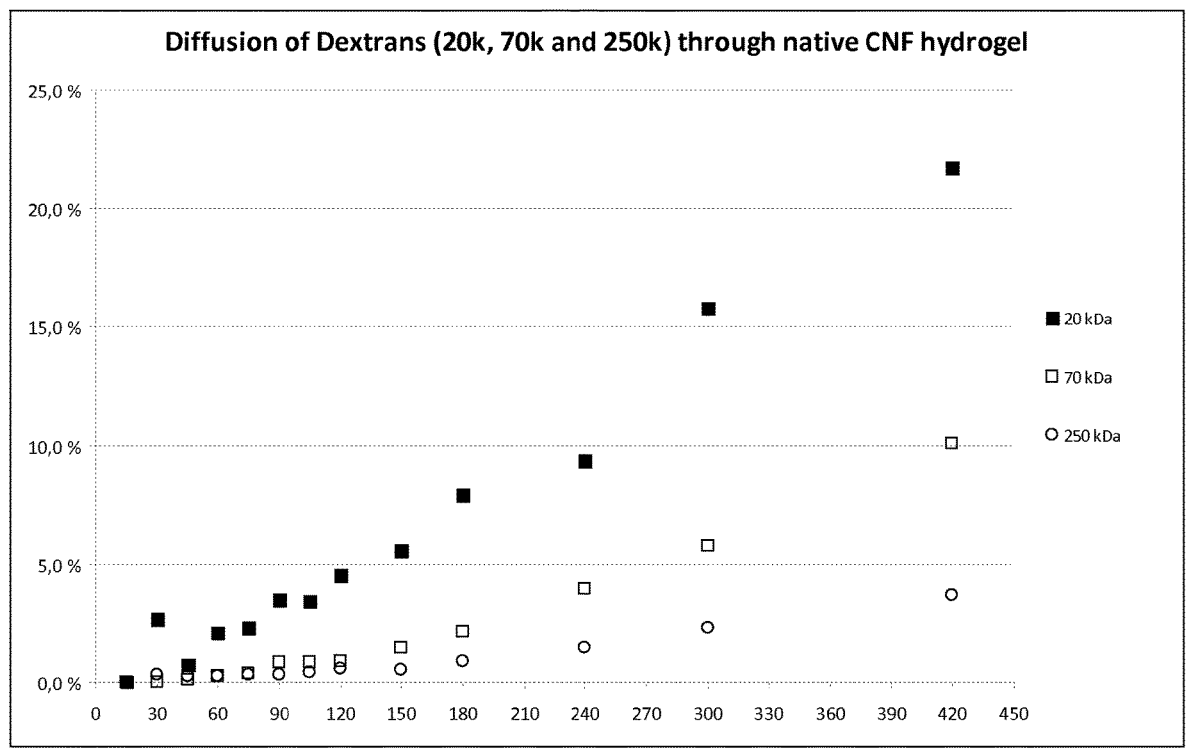
FIG. 4 depicts diffusion of different molecular weight dextrans (20 kDa, 70 kDa, and 250 kDa) through 1% native cellulose nanofiber hydrogel.

Diffusion of different molecular weight dextrans through 1% native cellulose nanofiber gel is presented in FIG. 4. The diffusion of the model compounds takes place at constant rate and it is highly dependent on the molecular weight (size) of the compound. It is clear that in the CNF hydrogels molecules are able to diffuse efficiently although the gel structure is firm enough to stabilize the cell suspension.

The observed diffusion profile can be also utilized in various drug delivery formulations and applications. The diffusion of drugs can be controlled as a function of the size of the drug molecule or protein (used as drug) or as a CNF hydrogel concentration. The clear sustained release profile is especially beneficial for certain treatments where longer release is preferred, especially in the case of peptide or protein drugs.

Example 5

Proliferation of ARPE19 Cells on CNF Membrane

Native CNF membrane was placed in the bottom of a 96 well tissue culture plate and cell suspension in maintenance growth media containing 25,000-50,000 cells per well were seeded on top of the membrane. Membrane concentration ranges from 1.6 to 0.01%. Cell viability and proliferation was measured as a function of days after culturing the cells on the native CNF membrane in an incubator at 37 C in 5% $CO_2$ and 95% relative humidity.

Figure 5:
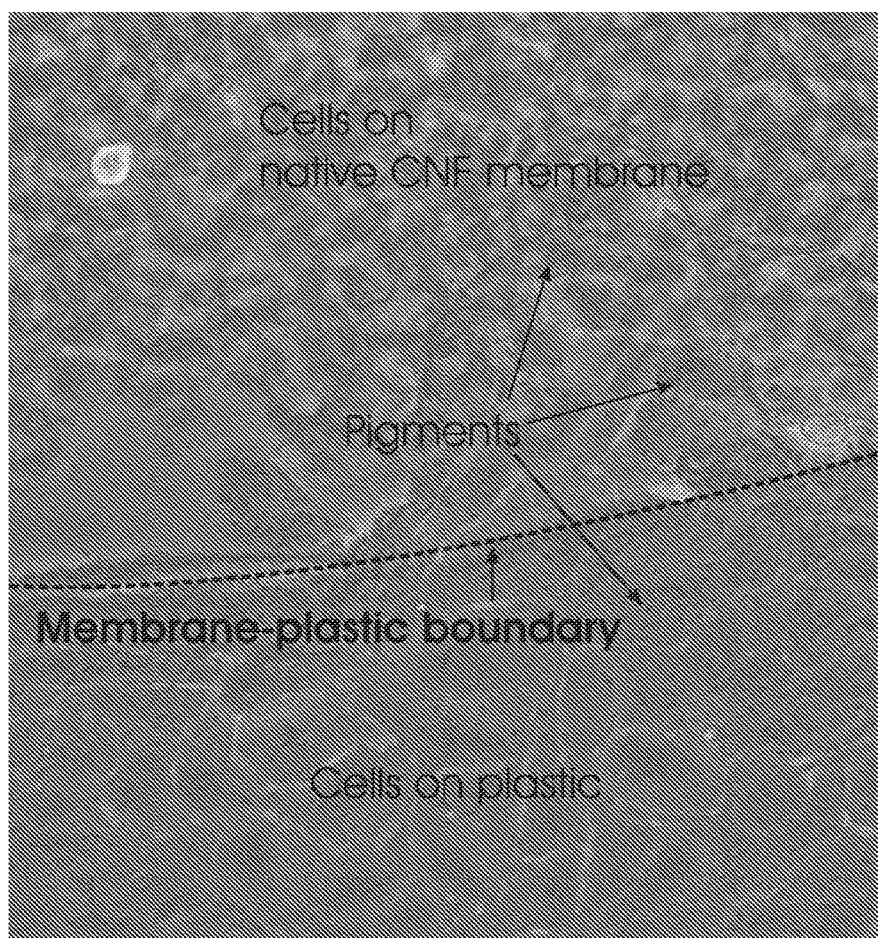
FIG. 5 depicts light microscopy image of ARPE-19 cells on native CNF membrane. The CNF membrane supports the growth of the cells on the upper part of the image, on lower part of the image the cells grow on cell culture plastic. Magnification 20×.

ARPE-19 cells on native CNF membrane were imaged with light microscopy. The CNF membrane supports the growth of the cells on the upper part of the image (FIG. 5) showing that ARPE-19 cells can be grown 2D on CNF membrane and that CNF membrane is useful as 2D cell growth matrix.

ARPE-19 cells proliferated well in hydrogels independently of the cell concentration used. There is no significant difference between the hydrogels. Cell proliferation increased ~2 fold when cultured on hydrogel as compared to cells cultured in absence of hydrogel.

Example 6

Morphology of 3D Cultured HepG2 Cell Clusters
Confocal Laser Microscopy

Figure 6:
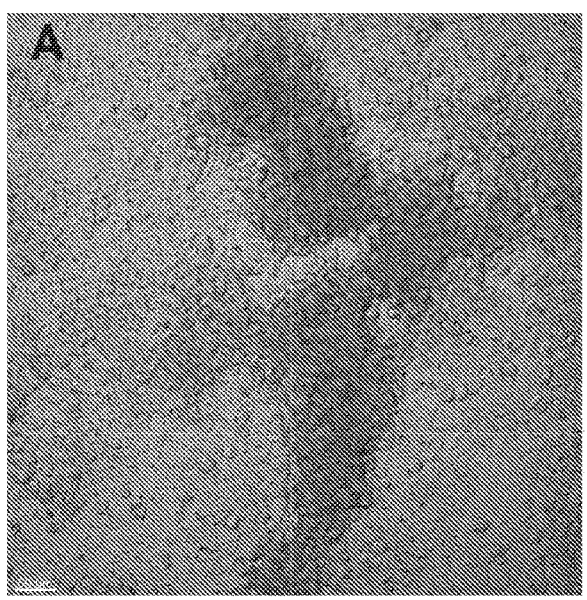
FIG. 6 depicts confocal microscopy section images of HepG2 cells on a cell culture plastic (A) and in the native cellulose nanofiber hydrogel (B).
Figure 6:
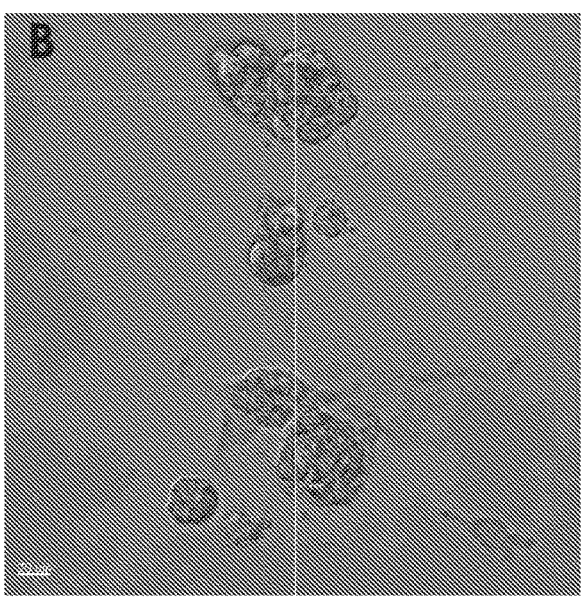

Laser confocal microscopy was used for live cell imaging. The spheroid shape of the encapsulated HepG2 cells in the CNF hydrogel clearly suggests that the cells are trapped within the hydrogel and are growing in three dimensions (FIG. 6). Images taken from cells after 5 days of culture are presented in FIG. 6 showing that the cells are viable within the 3D spheroids in both of the hydrogels. The viability of the cells was independent on the concentration of cells in hydrogels and the size of the spheroids increased as a function of time in all of the cultures (FIG. 6).

The medium was refreshed after every 48 h and the spheroid size increases as a function of time in the culture. When fibronectin was added to the CNF hydrogel, the viability of cells within the 3D spheroid was increased. Live/dead staining confocal microscopy images revealed that the cells remained viable during the 5 day period of culture. These findings are in relation to Alamar blue cell proliferation assay results (FIG. 2). This observation supports our hypothesis that CNF hydrogel mimics human ECM components. It has all the key compositions of ECM except fibronectin. Therefore addition of fibronectin improves the cell viability in 3D clusters. Fibronectin facilitated HepG2 cell attachment and viability. Fibronectin has earlier been shown to increase hepatocyte survival and to decrease apoptosis via binding to integrin β1.

By this way it is possible to show 3D structure of the HepG2 cells obtained without any other supporting material or ECM components than CNF hydrogel solely. This proves the usefulness and easy to use the CNF hydrogel as 3D cell culture matrix.

Example 7

Gel Strength

Figure 7:
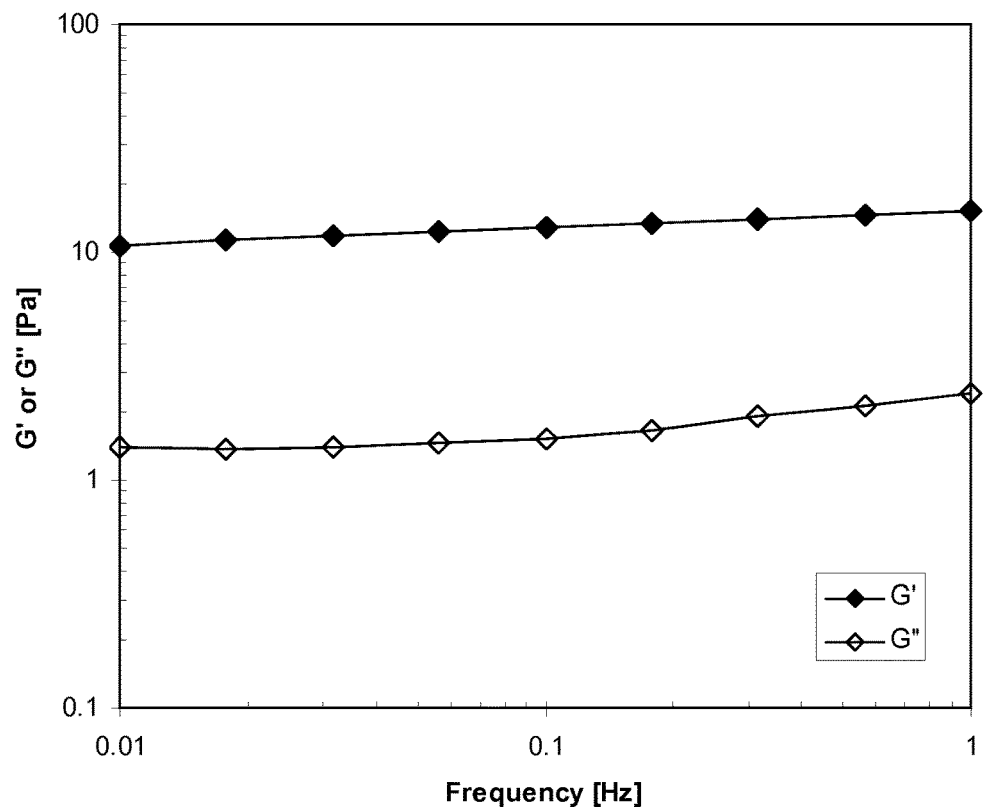
FIG. 7 depicts viscoelastic properties of 0.5% CNF hydrogel by dynamic oscillatory rheological measurements. Frequency dependence of G' (the storage modulus) and G" (the loss modulus) of a 0.5% native CNF hydrogel are presented.

An important function of a 3D cell culture medium is to keep cells homogeneously suspended in the matrix and prevent sedimentation. CNF fulfills this demand by its ability to form a gel network at very low concentration (0.5%). The gel-like structure of CNF was shown by determining its viscoelastic properties by dynamic oscillatory rheological measurements. The results of the frequency sweeps show typical gel-like behaviour. The storage modulus (G') is several orders of magnitude higher than the loss modulus (G') and nearly independent of frequency, which means that elastic (solid-like) properties are more pronounced than viscous (liquid-like) characteristics (FIG. 7). Typical for gels is also that both G' and G" are relatively independent of frequency. The viscoelastic properties of the CNF gels were determined with an oscillatory frequency sweep measurement in a rheometer (AR-G2, TA Instruments) at a strain of 0.1%.

Example 8

Flow Properties of CNF Hydrogel

The rheological flow properties of CNF hydrogels shows several features that are beneficial in the cell culture use. The hydrogels have a high viscosity at low shear (or rest) for optimum suspending capacity of the cells but also show shear-thinning behavior at higher shear rates to enable easy dispensing and injection. The ability of CNF to provide these kinds of rheological properties was demonstrated in a test series where the viscosity of CNF dispersions was measured over a broad shear stress (rate) range in a rotational rheometer (AR-G2, TA Instruments, UK).

Figure 8:
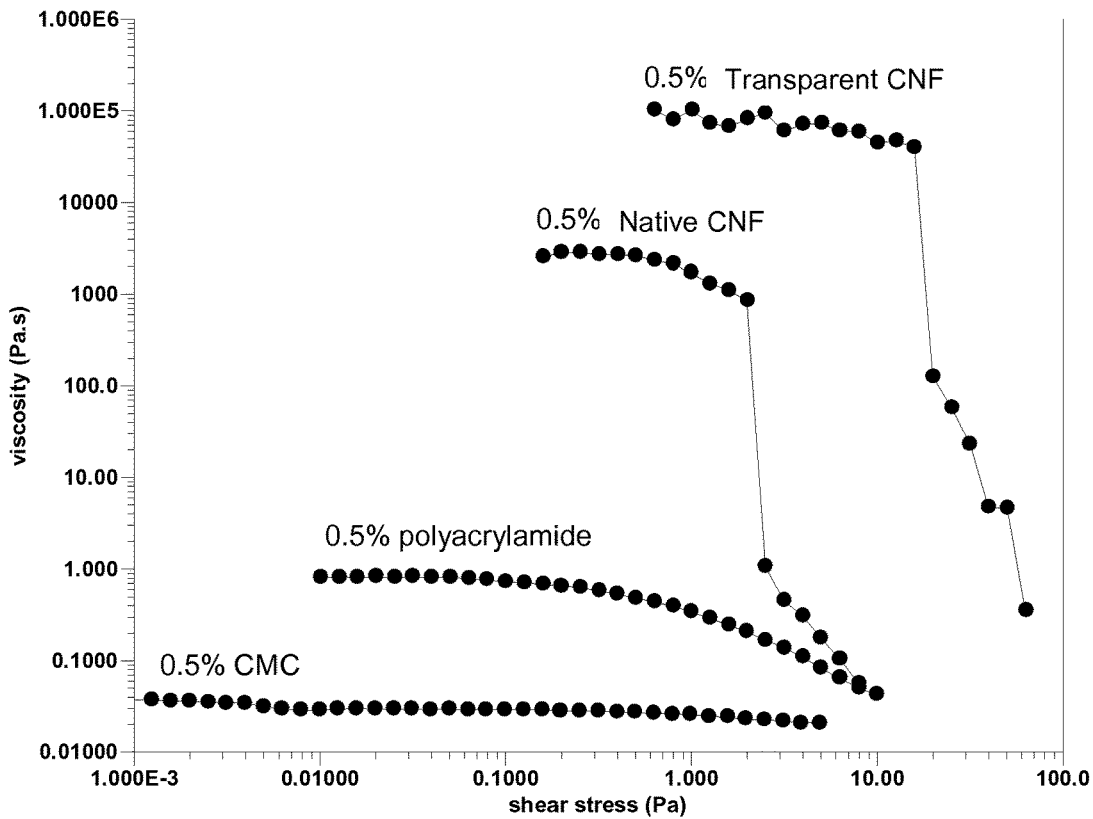
FIG. 8 depicts viscosity of 0.5% CNF hydrogels as function of applied shear stress in comparison with 0.5% solution of water soluble polymers polyacrylamide (5 000 kDa) and CMC (250 kDa).

CNF dispersions show much higher zero-shear viscosities (the region of constant viscosity at small shear stresses) than other water soluble polymers, as shown in FIG. 8. The zero-shear viscosity of CNF is greatly increased by smaller nanofibril diameter induced by preceding chemical pretreatment of the starting material. The stress at which shear-thinning behavior starts ("yield stress") is also considerably high for the CNF dispersions. The suspending ability of a material is the better the higher the yield stress. The cells are effectively stabilized against sedimentation by the combined effects of high zero-shear viscosity and high yield stress and high storage modulus. The gravitational force applied by the cells is much weaker than the yield stress. Thus, the suspended cells are "frozen" inside the gel matrix if mixing with CNF or "frozen" on the gel if deposited on the top of the gel.

Figure 9:
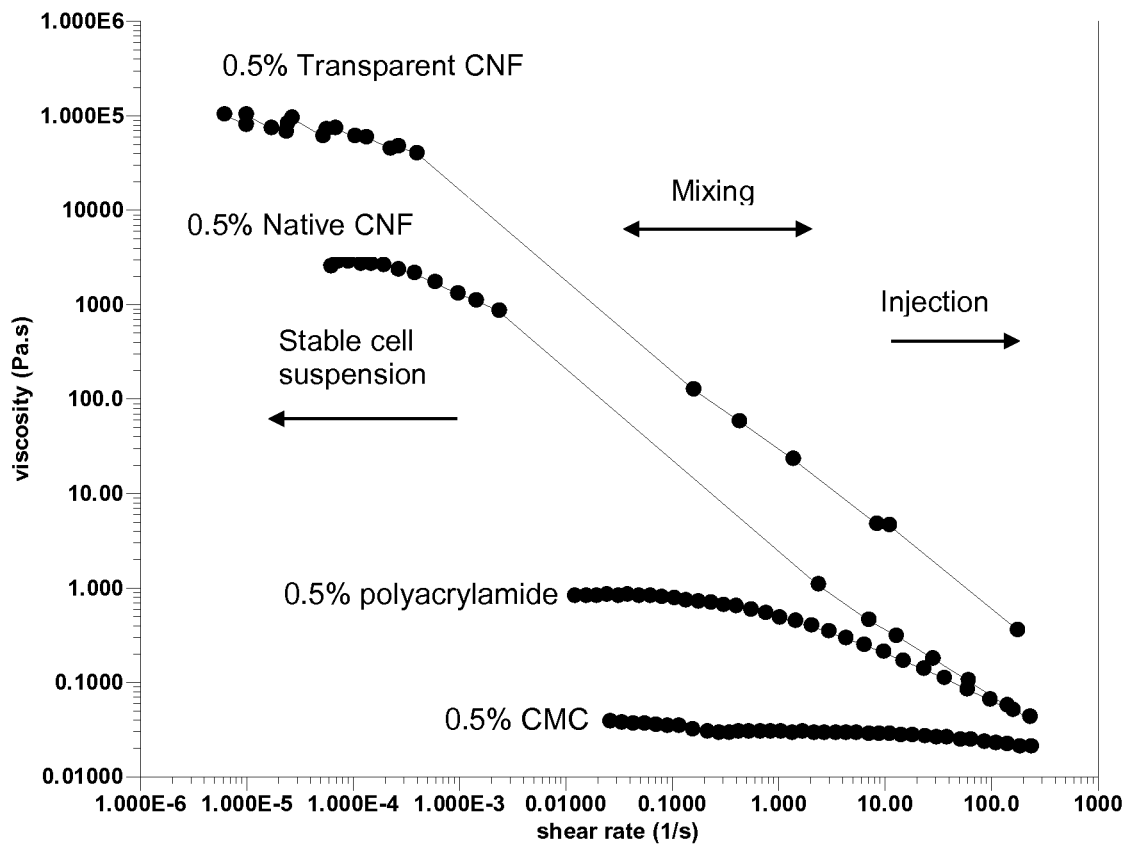
FIG. 9 depicts viscosity of 0.5% CNF hydrogels as function of measured shear rate in comparison with 0.5% polyacrylamide and CMC. Typical shear rate regions of different physical processes have been marked on the figure with arrows.

In FIG. 9 the viscosity is presented as a function of the measured shear rate. From this FIG. 9 it is obvious that the viscosity of the CNF dispersions drops at relatively small shear rates and reaches a similar level as that measured for the reference materials at shear rates of about 200 s-1.

Figure 10:
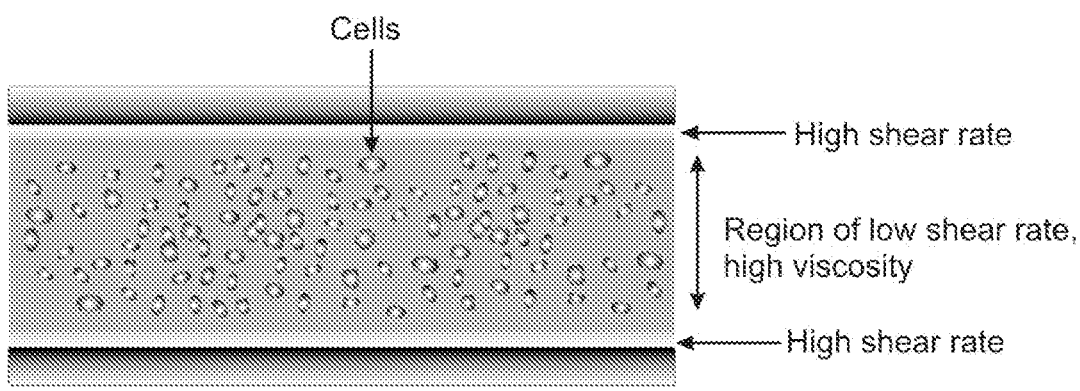
FIG. 10 depicts schematic presentation of a cell containing CNF hydrogel flowing in a needle. High shear rate region (low viscosity) is located at the gel-needle interface and low shear rate region (very high viscosity) is located in the middle of the needle.

The network structure of CNF breaks down upon shearing (FIG. 7). Upon the application of a certain stress, the viscosity of the system drops dramatically and a transition from solid-like to liquid-like behavior occurs. This kind of behavior is beneficial as it enables mixing of the cells homogeneously into the CNF suspension by moderate mechanical shearing. When two-phase liquids, such as flocculated CNF dispersions, are sheared (e.g. in a rheometer or in a tube), the dispersed phase tends to move away from the solid boundaries, which leads to the creation of a lower-viscosity layer of liquid at the walls of the container (FIG. 10). This phenomenon means that the resistance to flow, i.e. the viscosity is lower at the boundaries than in the bulk of the dispersion (Barnes, 1995). Respectively, injection of the CNF hydrogel with a syringe and a needle or with pipette is easy even at high concentrations (1-4%). The phenomenon enables also easy dispensing of cell suspensions with minimum disturbance of the cells, i.e. majority of the cells are located in the middle of the needle and are practically at rest (FIG. 10).

An easy injectability of the CNF hydrogels is also important feature when injectable formulations are considered. As was described in Example 6, the CNF hydrogels have release profiles that could be utilized in sustained and controlled drug release applications. These two findings for CNF hydrogels enable various potential drug treatment applications, like intraocular, intramuscular, subcutaneous treatments or for example viscoelastic eye drop formulations.

Example 9

Structure Recovery after Shearing has Ceased

An additional important rheological property of CNF hydrogels is that the high level of viscosity is retained after shearing (e.g. injection or mixing) has ceased. The structure recovery of a CNF dispersion was demonstrated by a test series where the material was first sheared in a rheometer (StressTech, Reologica Instruments Ab) at a high shear rate and after stopping the shear the recovery of the gel strength (G') was monitored with an oscillatory time sweep measurement. The shearing cycle was performed in a concentric cylinder geometry at a constant stress of 40 Pa for 61 s. The evolution of shear rate and viscosity during this test is shown in FIG. 10. The material was sheared at a relatively high shear rate (1000 s-1) for a time period of at least 40 s, during which the viscosity of the material dropped below 40 mPa s.

After stopping the shear, the evolution of G' (a measure of gel strength) was followed by an oscillatory measurement at constant frequency (1 Hz) and small stress (0.5 Pa). The measurement was started exactly 10 s after the shearing was stopped. From FIG. 11 it is obvious that a gel network is very rapidly formed when the CNF dispersion is allowed to rest after it has been sheared at high shear rates. Substantial structure recovery is observed already 10 s after the cessation of shear (equal to time zero in FIG. 11). A constant storage modulus (G') level is reached after keeping the CNF dispersion at rest for less than 10 min. The G'-level that the extensively sheared CNF dispersion developed was comparable to that of a CNF dispersion that was only gently mixed with a glass rod before the structure recovery test.

Figure 11:
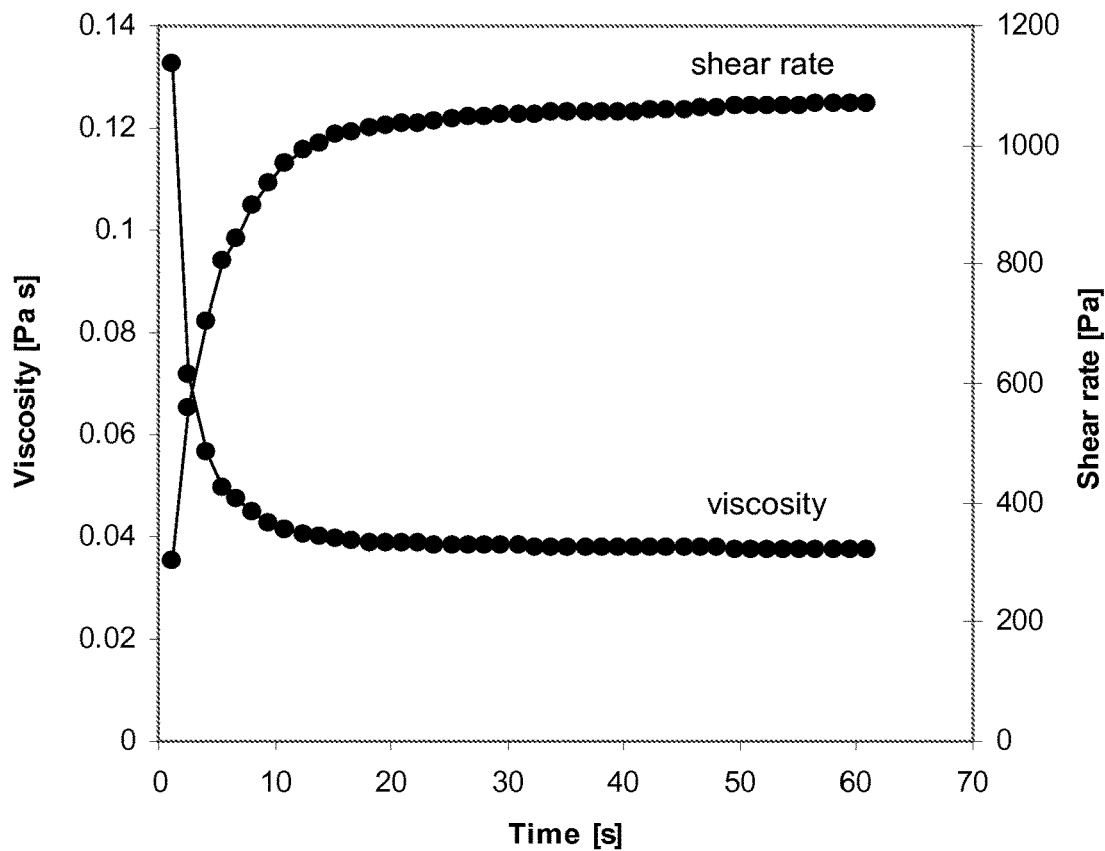
FIG. 11 depicts evolution of shear rate and viscosity when a 0.7% native CNF hydrogel was sheared in a rheometer in concentric cylinder geometry at a constant stress of 40 Pa.

Evolution of shear rate and viscosity when a 0.7% native CNF dispersion was sheared in a rheometer in concentric cylinder geometry at a constant stress of 40 Pa is presented in FIG. 11.

Figure 12:
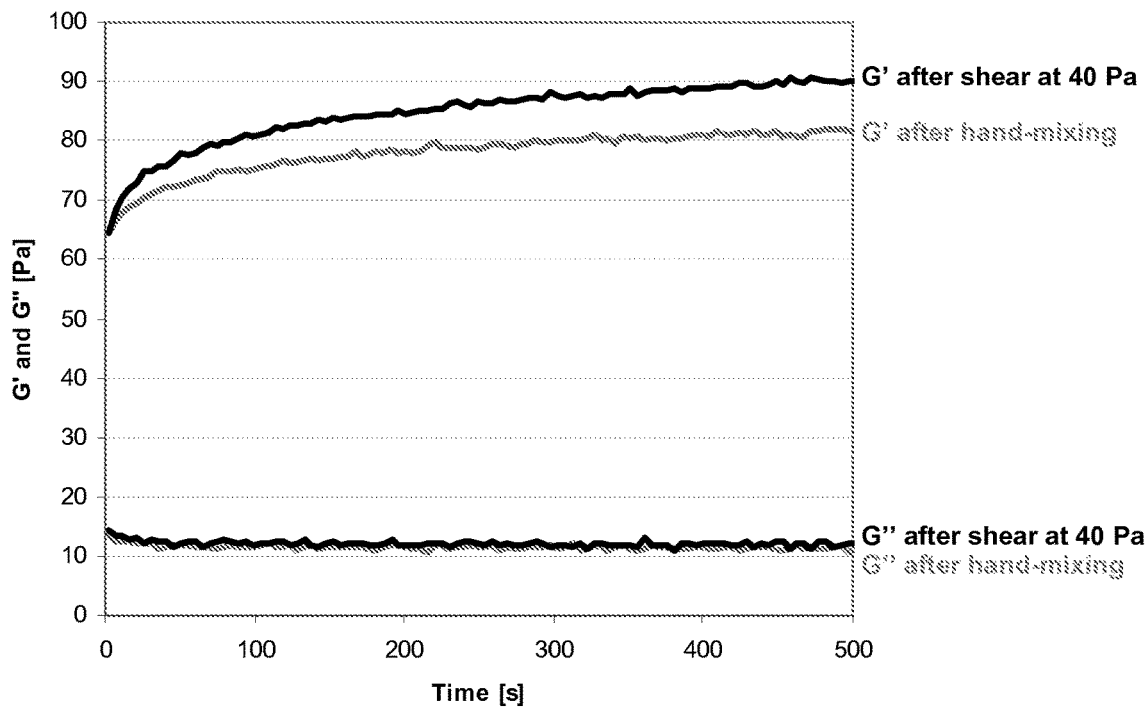
FIG. 12 depicts structure recovery of a 0.7% native CNF hydrogel dispersion after shearing at high shear-rate as compared with after gentle mixing with a glass rod.

Structure recovery of a 0.7% native CNF dispersion after shearing at high shear-rate as compared with after gentle mixing with a glass rod is presented in FIG. 12.

The fast structure recovery is important for hydrogel-type cell culture materials for two reasons. Firstly, it enables cells to be homogeneously distributed in the CNF hydrogels after mixing them with the hydrogel. Secondly, if the CNF hydrogels are used to transport cultured cells, the fast recovery of the gel structure effectively traps the cells to the desired place and the migration is minimal, for example when in cell transplantation is considered. Fast recovery is essential also in the injectable drug release formulations.

Example 10

Stability

As was shown in Example 1, even very dilute dispersions of CNF have a very high viscosity at low shear rates. The hydrogel structure is also recovered when shear, such as injection, ceases. At static conditions, CNF forms a hydrogel network with high elastic modulus and exceptionally high yield stress. Due to these properties, CNF has a very high suspending power of solid particles even at very low concentration.

Figure 13:
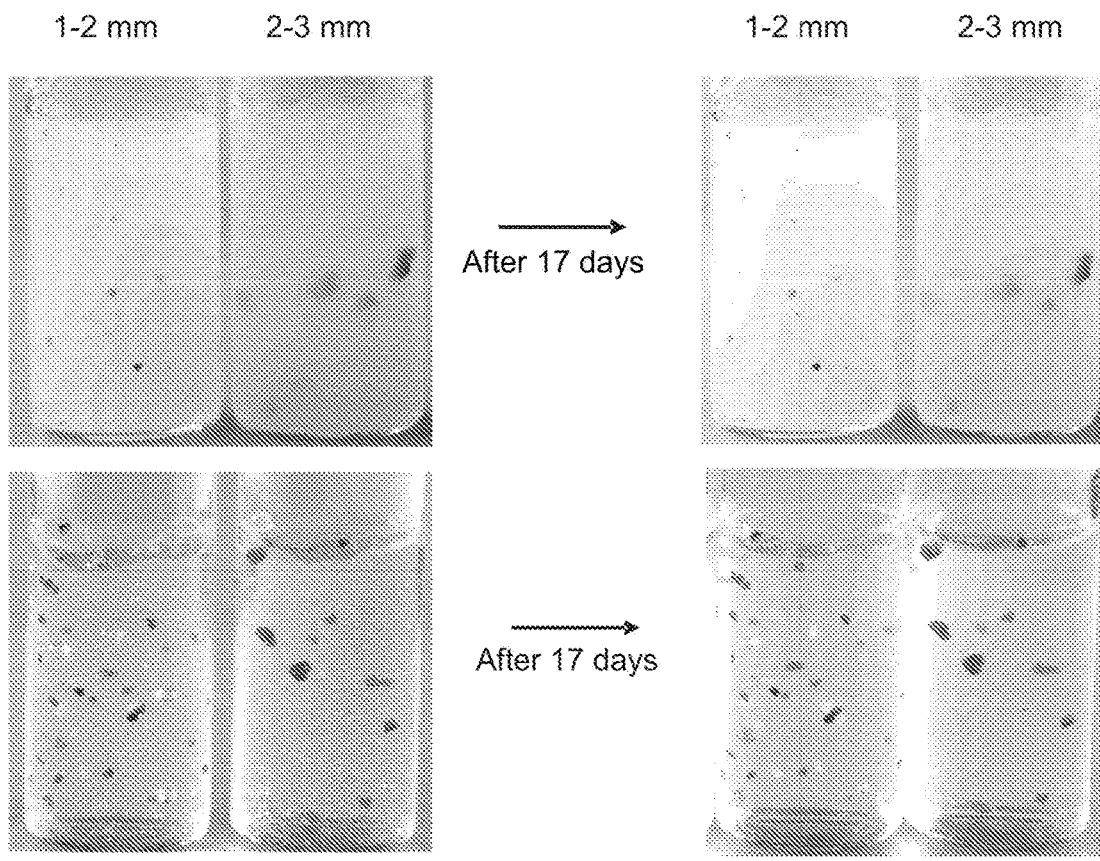
FIG. 13 depicts stability of two gravel suspensions in 0.5% native CNF hydrogel, (top row) and in 0.5% transparent CNF hydrogel (bottom row) for 17 days period. The gravel was CEN Standard sand (EN 196-1) with average particle size 1-2 mm and 2-3 mm. The samples were stored at room temperature.

The suspending ability at static conditions is demonstrated with gravel suspensions. 0.5% dispersions of native CNF and transparent CNF are able to stabilize even 2-3 mm size gravel particles for very long periods of time, see FIG. 13. It should be noted that the transparent CNF is able to stabilize particle suspensions at lower concentration than native CNF.

Example 11

Enzymatic Hydrolysis

It is commonly known that certain enzymes, cellulases, are able to hydrolyse β-(1-4)-bonds in cellulose. For example endo-1,4-β-glucanases (EGs) that target cellulose chains in random locations away from the chain ends; exoglucanases or exocellobiohydrolases (CBHs) that degrade cellulose by splitting off molecules from both ends of the chain producing cellobiose dimers; and β-glucosidases (BGLs) that hydrolyze the cellobiose units (produced during EG and CBH attack) to glucose. Respectively, cellulose nanofibers can be enzymatically hydrolyzed to glucose with an aid of cellulases (Ahola, S., Turon, X., Österberg, M., Laine, J., Rojas, O. J., Langmuir, 2008, 24, 11592-11599).

Enzymatic hydrolysis of cellulose can be utilized in cellulose nanofiber containing cell culture systems for various reasons. Upon the hydrolysis of CNF hydrogel, the viscosity of the media is drastically lowered and the cultured cell structures are easily accessible e.g. for staining. Also, after the hydrolysis, the cell structures can be transferred or transplanted without the cellulose containing material. The degradation product, glucose, is generally non-toxic to cells and can be utilized as a nutrient in cell culturing.

Figure 14:
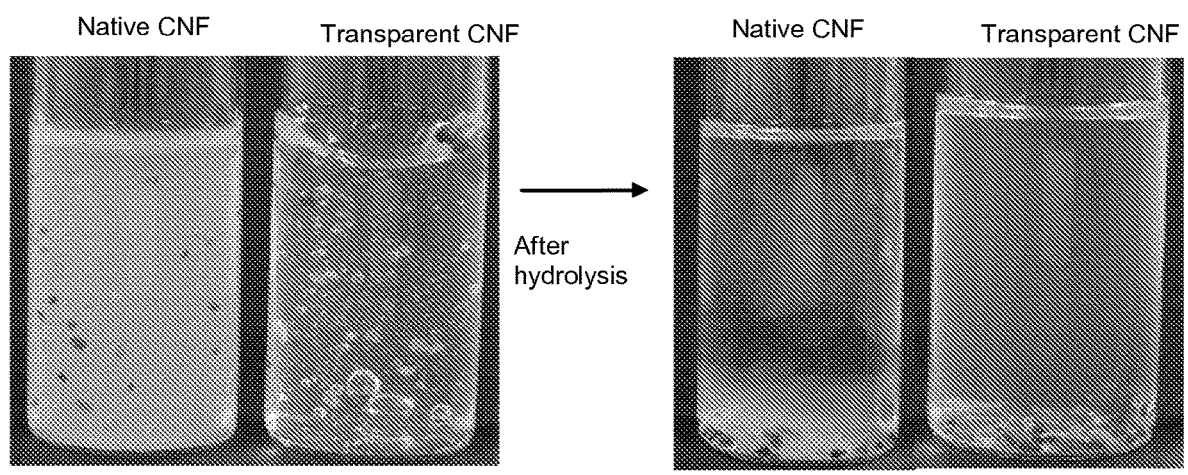
FIG. 14 depicts the influence of enzymatic hydrolysis on the suspension ability of cellulose nanofiber gels. The gravel was CEN Standard sand (EN 196-1) with average particle size 1-2 mm.

The enzymatic hydrolysis of cellulose nanofibers can be conducted with an aid of different cellulases at different environment. In FIG. 14, the effect of commercial Celluclast enzymes on the suspending power of the gels is demonstrated. Both native and transparent CNF hydrogels loose the suspending power due to enzymatic degradation of the gel structure. The cultured cell lines can be also genetically engineered to produce the needed enzyme protein into the culture system.

The invention claimed is:
1. A composition for cell culture or cell delivery, the composition comprising:
sterile, plant derived, mechanically disintegrated cellulose nanofibers and/or derivatives thereof, in a form of a three-dimensional hydrogel matrix having a nanofiber concentration ranging from about 0.01 to about 1.7 wt %, wherein the cellulose nanofibers and/or derivatives thereof are structurally type I cellulose; and a plurality of cells homogeneously distributed within the three-dimensional matrix.

2. The composition according to claim 1, wherein the diameter of cellulose nanofibers or nanofiber bundles in the cellulose nanofibers and/or derivatives thereof is less than 1 µm.

3. The composition according to claim 1, wherein the derivatives of the cellulose nanofibers comprise chemically or physically modified derivatives of a cellulose nanofiber or nanofiber bundles.

4. The composition according to claim 1, wherein the composition further comprises additives selected from the group consisting of extracellular matrix components, serum, growth factors and proteins.

5. The composition according to claim 1, further comprising an immobilized cell or an immobilized enzyme.

6. The composition according to claim 1, wherein the mechanically disintegrated cellulose nanofibers are acid-base pretreated.

7. The composition of claim 1, wherein the mechanically disintegrated cellulose nanofibers form a gel at 0.5% concentration.

8. The composition of claim 7, wherein the network structure of the cellulose nanofibers breaks down upon shearing.

9. The composition of claim 8, wherein network structure of the cellulose nanofibers reforms after shearing ceases.

10. The composition according to claim 1, wherein the at least one cell is a eukaryotic cell or a prokaryotic cell.

11. The composition according to claim 1, wherein the at least one cell is a stem cell.

12. The composition according to claim 1, wherein the cellulose nanofibers and/or derivatives thereof are inert and do not provide fluorescent background.

13. The composition according to claim 1, wherein the cell culture or cell delivery composition is injectable.

14. The composition according to claim 1, wherein the composition has a nanofiber concentration ranging from about 0.01 to about 1.0 wt %.

15. The composition according to claim 1, wherein the composition has a solid-like viscosity at rest and a liquid-like viscosity upon shearing.

16. A method for producing a composition according to claim 1, wherein said method comprises the steps of
providing microbially pure, plant derived, mechanically disintegrated cellulose nanofibers and/or derivatives thereof in a form of a two-dimensional or three-dimensional hydrogel matrix,
mixing together said cellulose nanofibers and/or derivatives thereof with water, and
providing living cells to the cellulose nanofibers,
wherein the cellulose nanofibers and/or derivatives thereof are structurally type I cellulose.

17. The method according to claim 16, wherein the method further comprises combining the mixture with a medicament.

18. The method according to claim 16, wherein the mechanically disintegrated cellulose nanofibers are acid-base pretreated.

* * * * *